United States Patent
Sato et al.

(10) Patent No.: US 10,941,242 B2
(45) Date of Patent: Mar. 9, 2021

(54) AMINE COMPOUND, AMINE COMPOSITION, AND EPOXY RESIN CURING AGENT

(71) Applicant: MITSUBISHI GAS CHEMICAL COMPANY, INC., Tokyo (JP)

(72) Inventors: Saeko Sato, Kanagawa (JP); Yuiga Asai, Kanagawa (JP); Tomotaka Wada, Kanagawa (JP); Takuma Hanaoka, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 23 days.

(21) Appl. No.: 16/090,998

(22) PCT Filed: Apr. 4, 2017

(86) PCT No.: PCT/JP2017/014017
§ 371 (c)(1),
(2) Date: Oct. 3, 2018

(87) PCT Pub. No.: WO2017/175740
PCT Pub. Date: Oct. 12, 2017

(65) Prior Publication Data
US 2019/0112416 A1    Apr. 18, 2019

(30) Foreign Application Priority Data
Apr. 6, 2016 (JP) .............................. JP2016-076896

(51) Int. Cl.
| | |
|---|---|
| C08G 59/50 | (2006.01) |
| C07C 211/27 | (2006.01) |
| C09D 163/00 | (2006.01) |
| C09J 163/00 | (2006.01) |
| C09K 3/10 | (2006.01) |
| C09D 7/40 | (2018.01) |
| C07C 209/60 | (2006.01) |
| C09J 11/06 | (2006.01) |
| C08G 59/56 | (2006.01) |
| C08K 5/00 | (2006.01) |
| C07B 61/00 | (2006.01) |

(52) U.S. Cl.
CPC ........ C08G 59/5033 (2013.01); C07C 209/60 (2013.01); C07C 211/27 (2013.01); C08G 59/50 (2013.01); C08G 59/56 (2013.01); C08K 5/0025 (2013.01); C09D 7/40 (2018.01); C09D 163/00 (2013.01); C09J 11/06 (2013.01); C09J 163/00 (2013.01); C09K 3/10 (2013.01); C07B 61/00 (2013.01)

(58) Field of Classification Search
None
See application file for complete search history.

(56) References Cited

U.S. PATENT DOCUMENTS

| | | | |
|---|---|---|---|
| 4,302,603 A | 11/1981 | Pez | |
| 2002/0055605 A1* | 5/2002 | Yonehama | ............ C07C 211/27 528/93 |
| 2005/0038298 A1 | 2/2005 | Echigo et al. | |
| 2005/0137424 A1 | 6/2005 | Kuwahara et al. | |
| 2009/0264593 A1* | 10/2009 | Volle | .................... C08G 59/188 525/185 |
| 2013/0303805 A1 | 11/2013 | Kuwahara et al. | |

FOREIGN PATENT DOCUMENTS

| | | |
|---|---|---|
| JP | 57-128659 A | 8/1982 |
| JP | 2002-161076 A | 6/2002 |
| JP | 2005-89455 A | 4/2005 |
| JP | 2005-179203 A | 7/2005 |
| JP | 2005-179204 A | 7/2005 |
| JP | 2008-503627 A | 2/2008 |
| JP | 2011-88863 A | 5/2011 |
| WO | 2012/105303 A1 | 8/2012 |

OTHER PUBLICATIONS

International Search Report in International Patent Application No. PCT/JP2017/014017, dated Jun. 27, 2017.
International Preliminary Report on Patentability in International Patent Application No. PCT/JP2017/014017, dated Oct. 9, 2018.

* cited by examiner

*Primary Examiner* — Megan McCulley
(74) *Attorney, Agent, or Firm* — Greenblum & Bernstein, P.L.C.

(57) ABSTRACT

Provided are an amine compound represented by the following formula (1), which has a low active hydrogen equivalent weight and thus is capable of providing a cured product having good properties because the amine compound has sufficient curability even though the amount of amine compound blended in an epoxy resin composition is small when the amine compound is used as an epoxy resin curing agent, and an amine composition and an epoxy resin curing agent, which contain the compound:

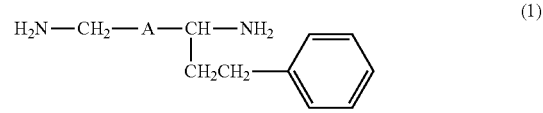

wherein A is a 1,2-phenylene group, a 1,3-phenylene group, or a 1,4-phenylene group.

15 Claims, 4 Drawing Sheets

[Fig. 3]
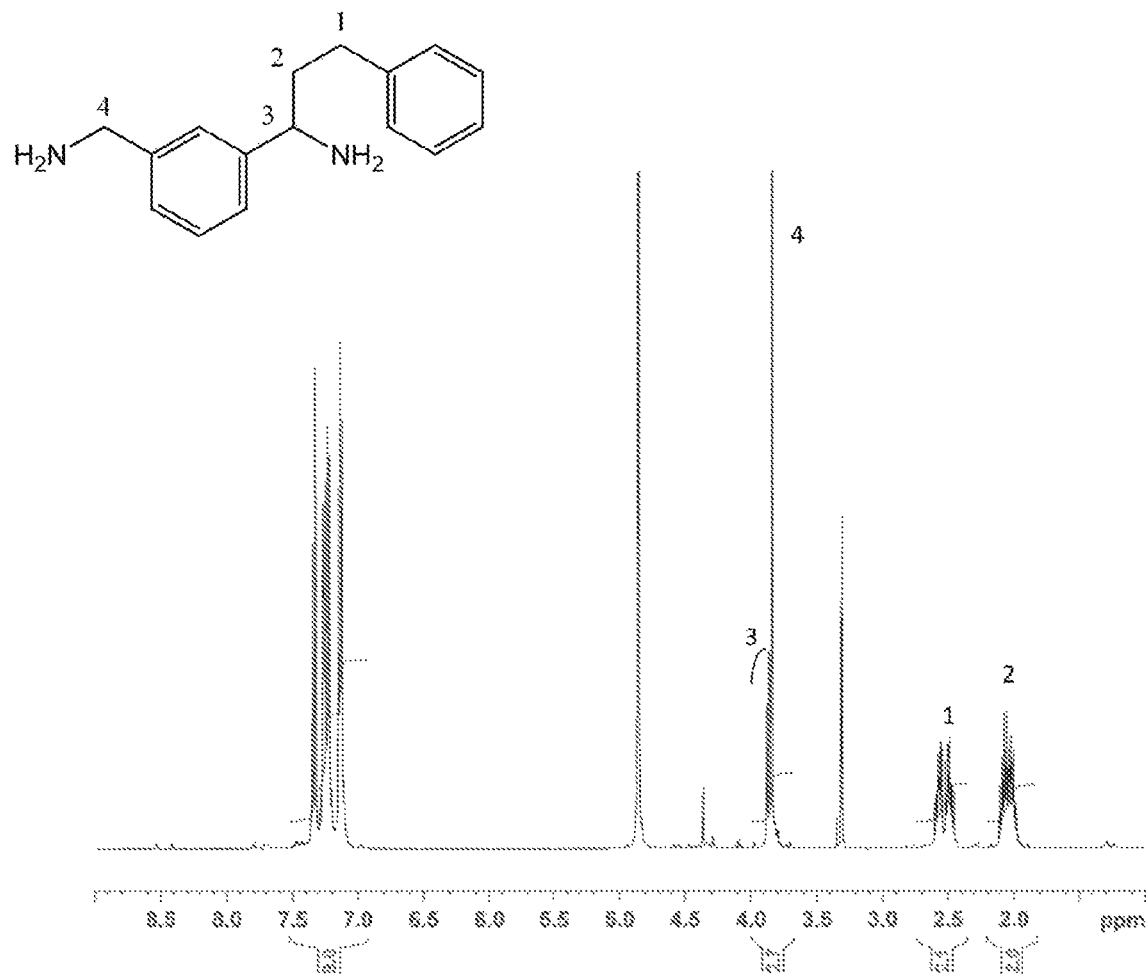

[Fig. 4]
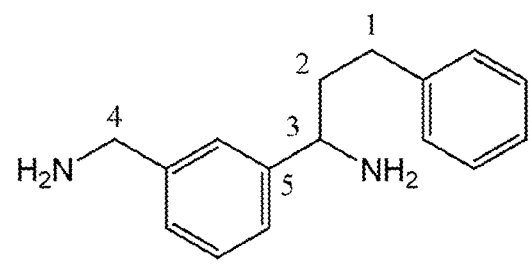
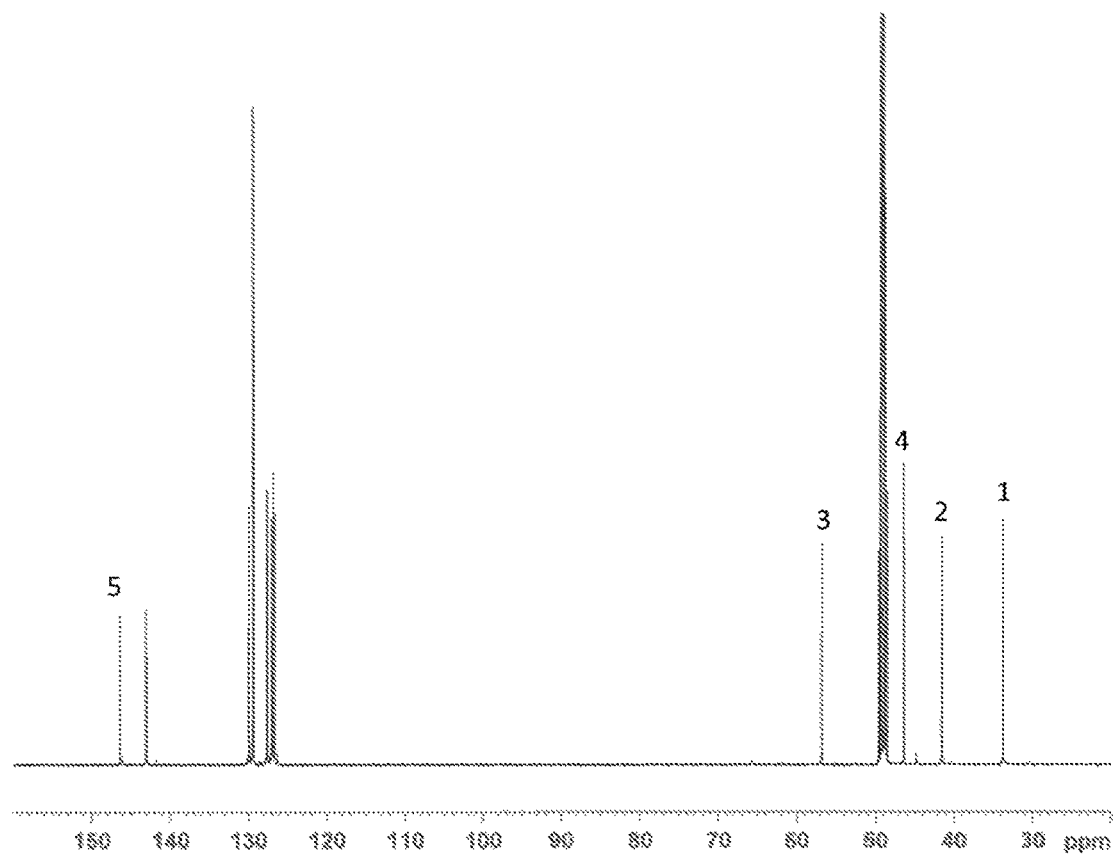

AMINE COMPOUND, AMINE COMPOSITION, AND EPOXY RESIN CURING AGENT

TECHNICAL FIELD

The present invention relates to a novel amine compound, and an amine composition and an epoxy resin curing agent, which contain the compound.

BACKGROUND ART

A polyamine, and a compound obtained by subjecting a polyamine and an alkenyl compound, an epoxy compound, or the like to addition reaction are known to be useful as an epoxy resin curing agent. An epoxy resin composition using the epoxy resin curing agent has been widely used in the paint fields, such as a corrosion-resistant paint for ships, bridges, iron structures on land and sea, and in the civil engineering construction fields, such as lining, reinforcement and repair materials of concrete structures, floor materials of buildings, lining of water supply and sewage systems, packing materials, and adhesives.

Among them, an amine compound obtained by subjecting a polyamine and an alkenyl compound to addition reaction has a relatively small content of unreacted polyamine and exhibits a low viscosity, so that an epoxy resin composition using an epoxy resin curing agent including the compound is capable of providing a cured product having good properties.

For example, PTL 1 discloses an amino compound obtained by subjecting a polyamine and an alkenyl compound to addition reaction, and a preparation method thereof. PTL 2 discloses a method which includes subjecting a polyamine and an alkenyl compound to addition reaction in the presence of a predetermined compound as a method of producing an amino compound having less odor stably.

Further, PTL 3 discloses a curing agent for an epoxy resin, which includes an adduct obtained by allowing a diamine or a polyamine to react with styrene.

PTL 1 discloses a structural formula of a compound obtained by an addition reaction in the case where a xylylene diamine or a bis(aminomethyl)cyclohexane is used as a polyamine, and styrene is used as an alkenyl compound (claim 2, Examples, and the like). However, since for the compound, since hydrogen (hereinafter, referred to as "active hydrogen") bonded to a nitrogen atom of an amino group of the polyamine is substituted with a group derived from an alkenyl compound, the number of active hydrogens is decreased as compared to the polyamine which is a raw material, and as a result, the active hydrogen equivalent weight (hereinafter, also referred to as "AHEW") is increased. Since an epoxy resin curing agent having a high AHEW inevitably contains a large amount of epoxy resin curing agent blended in the epoxy resin, not only the blending composition of the epoxy resin composition is limited, but also the cost becomes high.

CITATION LIST

Patent Literature

PTL 1: JP 2002-161076 A
PTL 2: WO 2012/105303
PTL 3: JP 2008-503627 A

SUMMARY OF INVENTION

Technical Problem

A problem to be solved by the present invention is to provide an amine compound which has a low active hydrogen equivalent weight and thus is capable of providing a cured product having good properties because the amine compound has sufficient curability even though the amount of amine compound blended in an epoxy resin composition is small when the amine compound is used as an epoxy resin curing agent, and an amine composition and an epoxy resin curing agent, which contain the compound.

Solution to Problem

The present inventors, and the like have found an amine compound having a specific structure, and also found that the problem may be solved when the amine compound and an amine composition containing the same are used as an epoxy resin curing agent.

That is, the present invention relates to the following [1] to [18].

[1] An amine compound represented by the following formula (1):

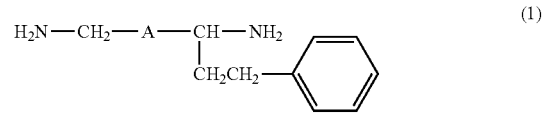

wherein A is a 1,2-phenylene group, a 1,3-phenylene group, or a 1,4-phenylene group.

[2] An amine composition containing the amine compound described in [1].

[3] The amine composition described in [2], wherein a content of the amine compound represented by the formula (1) is 6.0% by mass or more, and an active hydrogen equivalent weight of the amine composition is less than 100.

[4] The amine composition described in [2] or [3], further containing an amine compound represented by the following formula (2):

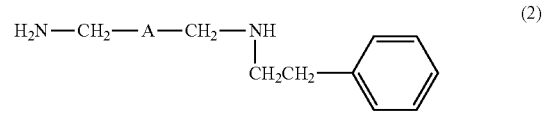

wherein A is the same as defined above.

[5] The amine composition described in [4], in which a content of the amine compound represented by the formula (1) is 15% by mass or more and less than 100% by mass based on 100% by mass of the total amount of the amine compound represented by the formula (1) and the amine compound represented by the formula (2).

[6] A method for preparing the amine compound described in [1], including:

subjecting a diamine represented by the following formula (3) and styrene to addition reaction in the presence of an alkali metal-containing catalyst selected from the group consisting of the following (c1) and the following (c2):

wherein A is the same as defined above.

(c1): one or more alkali metal amides selected from the group consisting of potassium amide, rubidium amide, and cesium amide, and (c2): a combination of an alkali metal amide with one or more selected from the group consisting of an alkali metal alkoxide, an alkali metal hydroxide, an alkali metal halide, and an alkali metal nitrate.

[7] A method for preparing the amine composition described in any one of [2] to [5], the method including:

subjecting diamine represented by the following formula (3) and styrene to addition reaction in the presence of an alkali metal-containing catalyst selected from the group consisting of the following (c1) and the following (c2):

wherein A is the same as defined above.

(c1): one or more alkali metal amides selected from the group consisting of potassium amide, rubidium amide, and cesium amide, and (c2): a combination of an alkali metal amide with one or more selected from the group consisting of an alkali metal alkoxide, an alkali metal hydroxide, an alkali metal halide, and an alkali metal nitrate.

[8] The method described in [6] or [7], wherein the alkali metal amide of (c2) is one or more selected from the group consisting of sodium amide and potassium amide.

[9] The method described in any one of [6] to [8], wherein the (c2) is a combination of an alkali metal amide with an alkali metal alkoxide, and the alkali metal alkoxide is potassium t-butoxide.

[10] The method described in any one of [6] to [9], wherein the alkali metal-containing catalyst is added portionwise in the addition reaction.

[11] An epoxy resin curing agent containing the amine compound of [1] or the amine composition described in any one of [2] to [5].

[12] Further, the epoxy resin curing agent described in [11], further containing a modified product of a polyamine compound as the other curing agent component.

[13] In addition, the epoxy resin curing agent described in [11] or [12], further containing a curing accelerator.

[14] The epoxy resin curing agent described in any one of [11] to [13], which is a curing agent for a water-based epoxy resin.

[15] An epoxy resin composition containing the epoxy resin curing agent described in any one of [11] to [14] and an epoxy resin.

[16] A paint containing the epoxy resin composition described in [15].

[17] An adhesive containing the epoxy resin composition described in [15].

[18] A cured product of the epoxy resin composition described in [15].

Advantage Effects of Invention

According to the present invention, by using an amine compound having a specific structure and an amine composition containing the same as an epoxy resin curing agent, even though an amount of epoxy resin curing agent blended in the epoxy resin composition is small, the epoxy resin curing agent has sufficient curability, so that it is possible to provide a cured product having good properties. The epoxy resin composition is suitably used for various paints such as a paint for corrosion resistance, an adhesive, a floor material, a sealant, and the like.

BRIEF DESCRIPTION OF DRAWINGS

FIG. 3 is a $^1$H-NMR spectrum of the compound (1-1).
FIG. 4 is a $^{13}$C-NMR spectrum of the compound (1-1).

DESCRIPTION OF EMBODIMENTS

[Amine Compound]

Figure 1:
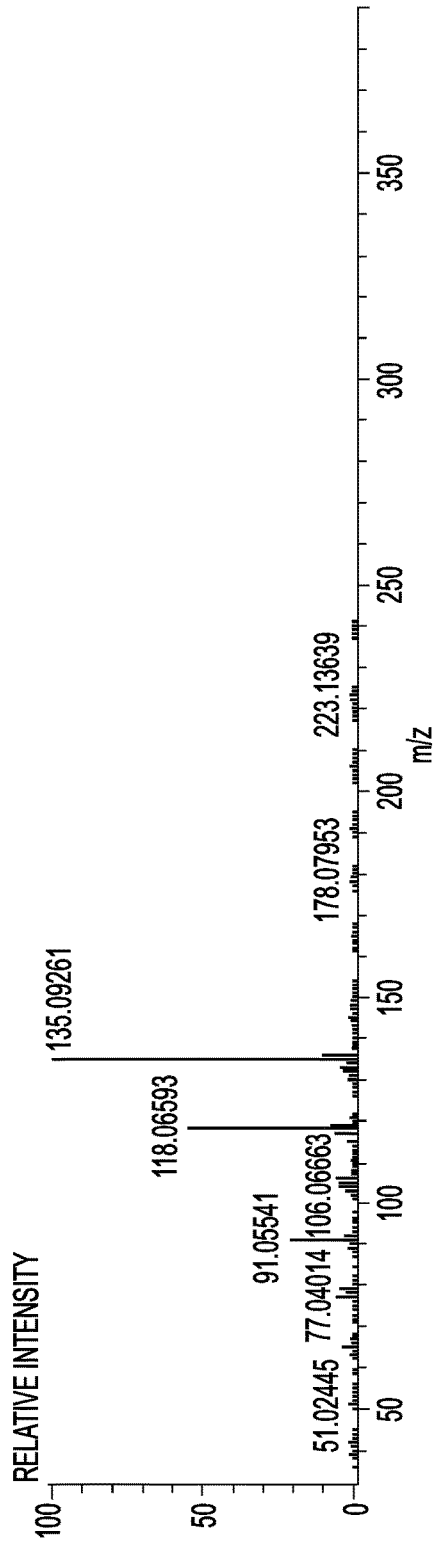
FIG. 1 is a chart of a mass spectrum when a GC-MS analysis is carried out on the amine compound (a compound (1-1) to be described below) of the present invention, which is obtained in Example A-1 on the EI+ mode.

An amine compound of the present invention is represented by the following formula (1).

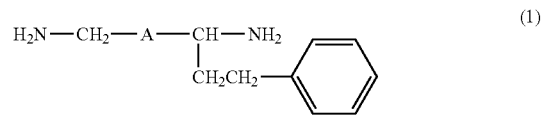

In the formula (1), A is a 1,2-phenylene group, a 1,3-phenylene group, or a 1,4-phenylene group. A is preferably a 1,3-phenylene group or a 1,4-phenylene group, and more preferably a 1,3-phenylene group.

The amine compound of the present invention is a compound obtained by subjecting a diamine (hereinafter, also referred to as "a raw material diamine") represented by the following formula (3) and styrene to addition reaction, and is a 1:1 adduct of the raw material diamine and styrene.

In the formula (3), A is the same as defined above.

The amine compound of the present invention has a structure in which hydrogen at a benzyl site of the raw material diamine represented by the formula (3) is substituted with a group derived from styrene. For this reason, all of the four active hydrogens derived from the raw material diamine remain in the amine compound of the present invention, so that the active hydrogen equivalent weight is lower than that of the compound having the structure disclosed in PTL 1. Accordingly, when the amine compound of the present invention and the amine composition containing the same are used as an epoxy resin curing agent, an amount of epoxy resin curing agent blended in the epoxy resin composition may be decreased as compared to that of the related art.

[Method for Producing Amine Compound]

It is preferred that a method for producing the amine compound of the present invention (hereinafter, also referred to as "the preparation method of the present invention") has a process of subjecting a diamine (a raw material diamine) represented by the following formula (3) and styrene to addition reaction in the presence of an alkali metal-containing catalyst selected from the group consisting of the following (c1) and the following (c2). The amine compound of the present invention, which is represented by the formula (1), may be efficiently and selectively produced according to the method.

wherein A is the same as defined above.

(c1) one or more alkali metal amides selected from the group consisting of potassium amide, rubidium amide, and cesium amide (c2) a combination of an alkali metal amide with one or more selected from the group consisting of an alkali metal alkoxide, an alkali metal hydroxide, an alkali metal halide, and an alkali metal nitrate The raw material diamine represented by the formula (3) is a xylylene diamine, and one or more selected from the group consisting of o-xylylene diamine, m-xylylene diamine (metaxylylene diamine; MXDA), and paraxylylene diamine (paraxylylene diamine; PXDA). Among them, one or more selected from the group consisting of m-xylylene diamine and paraxylylene diamine are preferred, and m-xylylene diamine is more preferred.

A catalyst used in the addition reaction of the raw material diamine and styrene is an alkali metal-containing catalyst selected from the group consisting of the (c1) and the (c2). Among them, by carrying out the addition reaction of the raw material diamine and styrene in the presence of any one of these catalysts, the reaction is efficiently performed, and further, the amine compound represented by the formula (1) may be obtained at a high selectivity.

The alkali metal-containing catalyst includes the predetermined alkali metal amide, so that the addition reaction of the raw material diamine and styrene is efficiently performed.

In addition, in the addition reaction of the raw material diamine and styrene, an amine compound represented by the following formula (2), besides the amine compound represented by the formula (1), may also be produced. However, the amine compound represented by the formula (1) may be obtained at a high selectivity by carrying out the addition reaction in the presence of the predetermined alkali metal-containing catalyst.

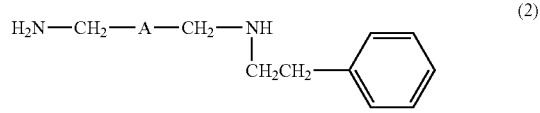

(2)

In the formula (2), A is the same as defined above.

Among them, it is preferred that the alkali metal-containing catalyst includes one or more of the compounds in which the alkali metal is potassium, rubidium, or cesium. When a catalyst including a compound in which the alkali metal is potassium, rubidium, or cesium is used, the amine compound of the present invention, which is represented by formula (1), may be obtained at a high selectivity. Among them, form the viewpoint of ease of availability, it is more preferred that the alkali metal-containing catalyst includes a compound (a potassium-containing compound) in which the alkali metal is potassium.

From the aforementioned viewpoint, when the alkali metal-containing catalyst used in the preparation method of the present invention is the (c1), it is preferred that one or more selected from the group consisting of potassium amide, rubidium amide, and cesium amide is used, and it is more preferred that potassium amide is used.

Further, when the alkali metal-containing catalyst is the (c2), it is preferred that the alkali metal contained in one or more compounds used among an alkali metal amide, an alkali metal alkoxide, an alkali metal hydroxide, an alkali metal halide and an alkali metal nitrate is one or more selected from the group consisting of potassium, rubidium, and cesium, and it is more preferred that the alkali metal is potassium. In particular, it is preferred that the alkali metal in the compound other than the alkali metal amide is one or more selected from the group consisting of potassium, rubidium, and cesium.

Among the alkali metal-containing catalysts used in the preparation method of the present invention, a content of the compound in which the alkali metal is potassium, rubidium, or cesium is preferably 10 mol % or more, more preferably 20 mol % or more, even more preferably 30 mol % or more, and still even more preferably 50 mol % or more in terms of mol % of the total amount of potassium, rubidium, and cesium, based on 100 mol % of the entire alkali metal in the alkali metal-containing catalyst, from the view point of obtaining the effect. Further, the upper limit thereof is 100 mol %.

Examples of the alkali metal amide in the (c2) include one or more selected from the group consisting of lithium amide, sodium amide, potassium amide, rubidium amide, and cesium amide. Among them, from the viewpoint of obtaining the amine compound represented by the formula (1) at a high selectivity, one or more selected from the group consisting of potassium amide, rubidium amide, and cesium amide are preferred. Meanwhile, from the viewpoint of ease of availability, one or more selected from the group consisting of lithium amide, sodium amide, and potassium amide are preferred, and in consideration of both the selectivity and the ease of availability of the amine compound represented by the formula (1), one or more selected from the group consisting of sodium amide and potassium amide are more preferred.

Examples of the alkali metal in the alkali metal alkoxide, the alkali metal hydroxide, the alkali metal halide, and the alkali metal nitrate in the (c2) include one or more selected from the group consisting of lithium, sodium, potassium, rubidium, and cesium. Among them, from the viewpoint of obtaining the amine compound represented by the formula (1) at a high selectivity, one or more selected from the group consisting of potassium, rubidium, and cesium are preferred, and from the viewpoint of ease of availability, potassium is more preferred.

Examples of the alkali metal alkoxide in the (c2) include one or more selected from the group consisting of lithium alkoxide, sodium alkoxide, potassium alkoxide, rubidium alkoxide, and cesium alkoxide, and from the viewpoint of obtaining the amine compound represented by the formula (1) at a high selectivity, one or more selected from the group consisting of potassium alkoxide, rubidium alkoxide, and cesium alkoxide are preferred, and from the viewpoint of ease of availability, potassium alkoxide is more preferred. The number of carbon atoms of the alkali metal alkoxide is preferably 1 to 6, more preferably 1 to 4, and even more preferably 2 to 4, from the viewpoint of reactivity.

Examples of the alkali metal alkoxide include methoxide, ethoxide, n-propoxide, isopropoxide, n-butoxide, i-butoxide, sec-butoxide, t-butoxide, and the like of one or more alkali metals selected from the group consisting of lithium, sodium, potassium, rubidium, and cesium. Among them, one or more selected from the group consisting of potassium methoxide, potassium ethoxide, potassium n-propoxide, potassium isopropoxide, potassium n-butoxide, potassium i-butoxide, potassium sec-butoxide, and potassium t-butoxide are preferred, and potassium t-butoxide is more preferred.

Examples of the alkali metal hydroxide in the (c2) include one or more selected from the group consisting of lithium hydroxide, sodium hydroxide, potassium hydroxide, rubidium hydroxide, and cesium hydroxide. Among them, from the viewpoint of obtaining the amine compound represented by the formula (1) at a high selectivity, one or more selected from the group consisting of potassium hydroxide, rubidium hydroxide, and cesium hydroxide are preferred, and from the viewpoint of ease of availability, potassium hydroxide is more preferred.

Examples of the alkali metal halide in the (c2) include one or more selected from the group consisting of fluoride, chloride, bromide, and iodide of one or more alkali metals selected from the group consisting of lithium, sodium, potassium, rubidium, and cesium, and among the halides, chloride is preferred.

As the alkali metal halide, one or more selected from the group consisting of potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide are more preferred, one or more selected from the group consisting of potassium fluoride, potassium chloride, potassium bromide, and potassium iodide are even more preferred, and potassium chloride is still even more preferred.

Furthermore, examples of the alkali metal nitrate in the (c2) include one or more selected from the group consisting of lithium nitrate, sodium nitrate, potassium nitrate, rubidium nitrate, and cesium nitrate. Among them, from the viewpoint of obtaining the amine compound represented by the formula (1) at a high selectivity, one or more selected from the group consisting of potassium nitrate, rubidium nitrate, and cesium nitrate are preferred, and from the viewpoint of ease of availability, potassium nitrate is more preferred.

In the (c2), the alkali metal alkoxide, alkali metal hydroxide, alkali metal halide, and the alkali metal nitrate may be used either alone or in combination of two or more thereof.

The (c2) is a combination of an alkali metal amide with an alkali metal alkoxide from the viewpoint of obtaining the amine compound represented by the formula (1) at a high selectivity, it is more preferred that the alkali metal alkoxide is potassium alkoxide, and it is even more preferred that the alkali metal alkoxide is potassium t-butoxide.

In the (c2), a ratio [(X):(Y)] of an amount (X) of the alkali metal amide to the total amount (Y) of the alkali metal alkoxide, the alkali metal hydroxide, the alkali metal halide, and the alkali metal nitrate is not particularly limited, but is preferably 1:0.05 to 1:20 by molar ratio, more preferably 1:0.1 to 1:10 by molar ratio, and even more preferably 1:0.2 to 1:5 by molar ratio, from the viewpoint of the balance between the reaction efficiency and the selectivity.

In the addition reaction of the raw material diamine and styrene, an amount of alkali metal-containing catalyst used is preferably 0.1 to 20 mol %, more preferably 0.5 to 15 mol %, even more preferably 1.0 to 12 mol %, and still even more preferably 1.5 to 10 mol % based on 100 mol % of the total amount of the raw material diamine and styrene, which are used. When the amount of alkali metal-containing catalyst used is 0.1 mol % or more, the addition reaction rate is good, and when the amount of alkali metal-containing catalyst used is 20 mol % or less, the amount is economically advantageous.

In the preparation method of the present invention, for an amount of styrene used for the raw material diamine, from the viewpoint of obtaining the amine compound represented by the formula (1) at a high selectivity, a molar ratio of styrene to 1 mol of the raw material amine ranges preferably from 0.1 to 5.0 mol, more preferably from 0.4 to 3.0 mol, even more preferably from 0.5 to 1.5 mol, and still even more preferably from 0.8 to 1.2 mol.

In the addition reaction of the raw material diamine and styrene, a method for adding the alkali metal-containing catalyst is not particularly limited, and any one of a whole addition and a divided addition may be used. Among them, it is preferred that the alkali metal-containing catalyst is added dividedly to the addition reaction of the raw material diamine and styrene. When the alkali metal-containing catalyst is added dividedly, the styrene reaction rate in the addition reaction is improved, and the coloration becomes decreased, so that an amine compound having a good color tone may be obtained. Further, when the alkali metal-containing catalyst is added dividedly, the catalyst active species easily remains in the reaction system for a long period of time, so that the addition reaction is performed with a smaller amount of catalyst.

When the alkali metal-containing catalyst is added dividedly, the number of divisions is not particularly limited, but ranges typically from 2 to 10 times, and preferably from 2 to 5 times from the viewpoint of workability.

In the preparation method of the present invention, it is preferred that the addition reaction of the raw material diamine and styrene is performed by bringing the raw material diamine and an alkali metal-containing catalyst into contact with each other in advance to perform a preliminary reaction, and then adding styrene thereto. By performing the preliminary reaction, the activity of the raw material diamine is increased, and the addition reaction with styrene is efficiently performed.

The preliminary reaction of the raw material diamine and the alkali metal-containing catalyst may be performed, for example, by charging the raw material diamine and the alkali metal-containing catalyst into a reactor, and heating the mixture while stirring under an inert atmosphere such as a nitrogen gas.

The temperature at the time of the preliminary reaction of the raw material diamine and the alkali metal-containing catalyst is preferably 50 to 140° C., and more preferably 70 to 100° C. When the preliminary reaction temperature is 50° C. or more, the raw material diamine is sufficiently activated, so that the subsequent addition reaction is efficiently performed. In addition, when the preliminary reaction temperature is 140° C. or less, it is possible to avoid the heat deterioration and the like of the raw material diamine.

The time for the preliminary reaction of the raw material diamine and the alkali metal-containing catalyst is preferably 20 to 360 minutes, and more preferably 30 to 120 minutes. When the time for the preliminary reaction is 20 minutes or more, the raw material diamine is sufficiently activated, so that the subsequent addition reaction is efficiently performed. Furthermore, when the time is 360 minutes or less, the time is advantageous in terms of productivity.

It is preferred that the preliminary reaction of the raw material diamine and the alkali metal-containing catalyst is performed, and then styrene is added thereto to perform an addition reaction with the raw material diamine. The method for adding styrene is not particularly limited, but it is preferred that styrene is added dividedly from the viewpoint of suppressing production of a polymeric product of styrene. Examples of the divided addition method include a method for adding styrene into a reactor by using a dropping funnel or a liquid feeding pump, and the like.

In the addition reaction of the raw material diamine and styrene, when the alkali metal-containing catalyst is added dividedly, for example, the following method may be adopted. First, after the preliminary reaction is performed by bringing the raw material diamine and a part of the alkali metal-containing catalyst into contact with each other by the above-described method, styrene is added to a preliminary reacted matter, and the remaining alkali metal-containing catalyst is added all at once or dividedly two or more times during the addition of styrene. When the number of divided additions of the alkali metal-containing catalyst is set to n, it is preferred that styrene is added to a preliminary reacted matter to which about (1/n) amount of the total amount of the alkali metal-containing catalyst is added, and in the step of adding about (1/n) amount of the total amount of styrene, a process of adding about (1/n) amount of the remaining alkali metal-containing catalyst is repeated (n−1) times.

The temperature at the time at the time of adding styrene, and at the time of the addition reaction is preferably 50 to 120° C., and more preferably, 70 to 100° C. When the reaction temperature is 50° C. or more, the addition reaction of the raw material diamine and styrene is efficiently performed. Further, when the reaction temperature is 120° C. or less, it is possible to suppress production of a polymeric product of styrene, which is a byproduct.

In addition, the time for the addition reaction is not particularly limited, and may be appropriately selected according to the type of catalyst used, the reaction condition, and the like. For example, the time for the addition reaction may be set to a time until an amount of unreacted styrene becomes 1% by mass or less by performing a sampling of the reaction solution during the addition reaction, and performing the quantification of unreacted styrene with gas chromatography, liquid chromatography, or the like. Typically, the time for the addition reaction is preferably 10 to 180 minutes, and more preferably 20 to 120 minutes after the addition of styrene is completed. When the time for the addition reaction is 10 minutes or more, an amount of unreacted raw material remaining is small, and when the time for the addition reaction is 180 minutes or less, the time is advantageous in terms of productivity.

In the obtained reaction solution, an amine compound produced by the reaction and the alkali metal-containing catalyst are included. Further, unreacted raw material diamine and unreacted styrene are also included in some cases.

The alkali metal-containing catalyst may be removed by filtration, washing, adsorption, and the like according to the type thereof. For example, when the alkali metal-containing catalyst is an alkali metal amide, the alkali metal amide is changed into an easily removable salt by adding an acid such as hydrochloric acid, hydrogen chloride gas, and acetic acid, an alcohol such as methanol and ethanol, water, or the like thereto, and then the salt can be filtered. For example, when water is used, the alkali metal amide becomes a hydroxide, which is easily filtered.

After the alkali metal-containing catalyst is removed from the reaction solution as described above, a mixture containing the amine compound represented by the formula (1) may be obtained by removing unreacted raw material diamine and unreacted styrene by distillation.

In the mixture, in addition to the amine compound represented by the formula (1), the amine compound represented by the formula (2), and an adduct such as a 1:2 adduct in which 1 mol of the raw material diamine and 2 mol of styrene are added, a 1:3 adduct in which 1 mol of the raw material diamine and 3 mol of styrene are added, and a 1:4 adduct in which 1 mol of the raw material diamine and 4 mol of styrene are added are included in some cases. In this case, the target compound may be isolated and purified by, for example, distillation, and the like.

[Amine Composition and Preparation Method Thereof]

The amine composition of the present invention contains the amine compound of the present invention, which is represented by the formula (1). Accordingly, the active hydrogen equivalent weight of the amine composition of the present invention may be lowered, and as a result, when the composition is used as an epoxy resin curing agent, even though an amount of epoxy resin curing agent blended in the epoxy resin composition is small, the epoxy resin curing agent has sufficient curability, so that it is possible to provide a cured product having good properties.

A content of the amine compound represented by the formula (1) in the amine composition of the present invention is preferably 6.0% by mass or more, more preferably 10% by mass or more, even more preferably 25% by mass or more, and still even more preferably 30% by mass or more. Further, the active hydrogen equivalent weight (AHEW) of the amine composition of the present invention is preferably less than 100, more preferably less than 90, even more preferably 85 or less, and still even more preferably 80 or less. When the content of the amine compound represented by the formula (1) in the amine composition and the AHEW of the amine composition are within the ranges, even though the amount of epoxy resin curing agent blended in the epoxy resin is small, the epoxy resin curing agent exhibits high curability when the composition is used as the epoxy resin curing agent. Further, from the viewpoint of economic feasibility, the AHEW of the amine composition of the present invention is preferably 65 or more, and more preferably 70 or more.

A content of the amine compound represented by the formula (1) in the amine composition may be obtained by a gas chromatography (GC) analysis, and specifically, may be obtained by the method described in the Examples. In addition, the AHEW of the amine composition may be measured by a titration method, and specifically, may be measured by the method described in the Examples.

The amine composition of the present invention may also contain an amine compound represented by the following formula (2).

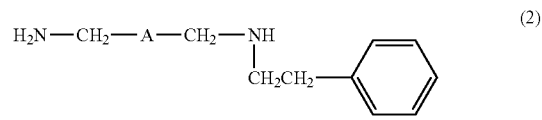

wherein A is the same as defined above.

When the amine composition of the present invention contains both the amine compound represented by the formula (1) and the amine compound represented by the formula (2), in the case of setting the total content of the amine compound represented by the formula (1) and the amine compound represented by the formula (2) to 100% by mass, the content [(1)/{(1)+(2)}] of the amine compound represented by the formula (1) is preferably 15% by mass or more, more preferably 30% by mass or more, even more preferably 40% by mass or more, still even more preferably 50% by mass or more, and preferably less than 100% by mass. When the content ratio [(1)/{(1)+(2)}] of the amine compound represented by the formula (1) is 15% by mass or more, the value of the AHEW of the amine composition is easily lowered, so that the curability when the composition is used as an epoxy resin curing agent is more improved.

The amine composition of the present invention may also contain a multi-adduct such as a 1:2 adduct of the raw material diamine and styrene and a 1:3 adduct of the raw material diamine and styrene. The multi-adduct also has active hydrogen, and the AHEW of the amine composition of the present invention is a value based on the total active hydrogen amount derived from the amine compound represented by the formula (1), the amine compound represented by the formula (2), the multi-adduct, and the like.

A method for producing the amine composition of the present invention is not particularly limited. For example, the amine composition of the present invention may be formulated by mixing the amine compound represented by the formula (1) with any component of the other amine compounds, and the like. Further, a mixture obtained by removing the alkali metal-containing catalyst or unreacted raw material from a reaction solution obtained after performing the addition reaction of the raw material diamine and styrene by the method which is the same as the method for producing the amine compound represented by formula (1) may also be used as it is as the amine composition of the present invention. That is, it is preferred that the amine composition of the present invention has a process of subjecting a diamine (a raw material diamine) represented by the following formula (3) and styrene to addition reaction in the presence of an alkali metal-containing catalyst selected from the group consisting of the following (c1) and the following (c2). By using the method, an amine composition containing a large amount of the amine compound represented by the formula (1) may be produced all at once.

$$H_2N-CH_2-A-CH_2-NH_2 \quad (3)$$

wherein A is the same as defined above.

(c1) one or more alkali metal amides selected from the group consisting of potassium amide, rubidium amide, and cesium amide, and (c2) a combination of an alkali metal amide with one or more selected from the group consisting of an alkali metal alkoxide, an alkali metal hydroxide, an alkali metal halide, and an alkali metal nitrate.

A preferred aspect in the method for producing the amine composition in this case is the same as that described in the method for producing the amine compound of the present invention. As described above, when a method for dividedly adding an alkali metal-containing catalyst in the addition reaction of the raw material diamine and styrene is adopted, the styrene reaction rate in the addition reaction is improved, and the coloration becomes decreased, so that an amine composition having a good color tone may be obtained.

The color tone of the amine compound and the amine composition of the present invention may be evaluated by measuring, for example, a Gardener color scale. From the viewpoint of obtaining a good color tone, each of the Gardener color scales of the amine compound and the amine composition preferably has a low value, and is preferably 10 or less, more preferably 8 or less, and even more preferably 5 or less. The Gardener color scale may be specifically measured by the method described in the Examples.

[Epoxy Resin Curing Agent]

The epoxy resin curing agent of the present invention contains the amine compound of the present invention or the amine composition of the present invention, which is described above.

When the amine compound of the present invention or the amine composition of the present invention is used for an epoxy resin curing agent, the amine compound or the amine composition may be used either alone as an epoxy resin curing agent and may be used in mixture with the other curing agent components such as other polyamines having an active hydrogen.

When the amine compound of the present invention is used for the epoxy resin curing agent, the amine compound may also be modified and used.

When the amine compound or the amine composition of the present invention is used for the epoxy resin curing agent, the amine compound or the amine composition may be used as a main component for the epoxy resin curing agent, and may be used in a small amount for the purpose of improving the performance of the epoxy resin curing agent. The "main component" as referred to herein refers to a component whose content is 50% by mass or more based on 100% by mass of the entire constituent components in the epoxy resin curing agent. Accordingly, the content of the amine compound or the amine composition of the present invention in the epoxy resin curing agent is not particularly limited, and may be set to, for example, 1% by mass or more, preferably 5% by mass or more, more preferably 10% by mass or more, even more preferably 20% by mass or more, still even more preferably 30% by mass or more, and still yet even more preferably 40% by mass or more. From the viewpoint of obtaining an epoxy resin composition capable of providing curability as a curing agent and a cured product having good properties, when the amine compound or the amine composition of the present invention is used as a main component for the epoxy resin curing agent, the content of the amine compound or the amine composition in the epoxy resin curing agent may be set to preferably 50% by mass or more, more preferably 60% by mass or more, even more preferably 70% by mass or more, still even more preferably 80% by mass or more, still yet even more preferably 90% by mass or more, further more preferably 95% by mass or more, and still further more preferably 99% by mass or more. Further, the upper limit thereof is 100% by mass.

Examples of the other curing agent component which may be used in the epoxy resin curing agent include a polyamine compound having at least two amino groups in the molecule thereof or a modified product thereof as a preferred component. As the "the other curing agent component," a modified product of the polyamine compound (hereinafter, also referred to as "a polyamine modified product") is preferred from the viewpoint of obtaining an epoxy resin composition capable of providing curability as a curing agent and a cured product having good properties. That is, when the epoxy resin curing agent of the present invention contains the other curing agent component in addition to the amine compound or the amine composition of the present invention, it is preferred that the epoxy resin curing agent of the present invention also contains a modified product of the polyamine compound as the the other curing agent component.

Examples of the polyamine compound include: a chain aliphatic polyamine compound such as ethylenediamine, diethylenetriamine, triethylenetetramine, tetraethylenepentamine, pentaethylenehexamine, and hexamethylenediamine; a polyamine compound having an alicyclic structure, such as 1,2-bis(aminomethyl)cyclohexane, 1,3-bis(aminomethyl)cyclohexane, 1,4-bis(aminomethyl)cyclohexane, menthene diamine, isophorone diamine, norbornane diamine, and 1,4-diamino-3,6-diethylcyclohexane; an aromatic polyamine compound such as phenylenediamine, diaminodiphenylmethane, and diaminodiphenylsulfone; a polyamine compound having a heterocyclic structure, such as N-aminomethylpiperazine and N-aminoethylpiperazine; a polyetherpolyamine compound; and the like, in addition to the diamine represented by the formula (3). These polyamine compounds may be used either alone or in combination of two or more thereof. Among them, as the polyamine compound, one or more selected from the group consisting of the diamine represented by the formula (3) and a polyamine compound having an alicyclic structure are preferred, and one or more selected from the group consisting of o-xylylene diamine, m-xylylene diamine, p-xylylene diamine, 1,2-bis(aminomethyl)cyclohexane, 1,3-bis(aminomethyl)cyclohexane, 1,4-bis(aminomethyl)cyclohexane, and isophorone diamine are more preferred.

Examples of the modified product of the polyamine compound include (i) a reaction product of a polyamine compound and an epoxy compound, (ii) a Mannich reaction product of a polyamine compound, a phenol-based compound, and an aldehyde compound, (iii) a reaction product of a polyamine compound and a carboxy group-containing compound, (iv) a product provided by a Michael addition reaction of a polyamine compound and an acrylic compound, and (v) a reaction product obtained by combining the (i) to the (iv).

Among them, as the modified product of the polyamine compound, one or more polyamine modified bodies selected from the group consisting of the (i) and the (iii) are preferred.

(i) Reaction Product of Polyamine Compound and Epoxy Compound (ii) Mannich Reaction Product of Polyamine Compound, Phenol-Based Compound, and Aldehyde Compound In the following description, the polyamine modified product of the (i) is referred to as "a polyamine modified product (i)," and the polyamine modified product of the (ii) is referred to as "a polyamine modified product (ii)."

<Polyamine Modified Product (i)>

The polyamine modified product (i) is a reaction product obtained by a reaction between a polyamine compound and an epoxy compound. Specific examples of the polyamine modified product (i) include a reaction product (hereinafter, also referred to as "polyamine modified product (i-1)") of a polyamine compound and epichlorohydrin, or a reaction product (hereinafter, also referred to as "polyamine modified product (i-2)") of a polyamine compound and a compound having at least two epoxy groups in the molecule thereof.

The polyamine compound used in the polyamine modified product (i) is the same as defined above, one or more selected from the group consisting of the diamine represented by the formula (3) and a polyamine compound having an alicyclic structure are preferred, and one or more selected from the group consisting of o-xylylene diamine, m-xylylene diamine, p-xylylene diamine, 1,2-bis(aminomethyl) cyclohexane, 1,3-bis(aminomethyl)cyclohexane, 1,4-bis (aminomethyl)cyclohexane, and isophorone diamine are more preferred. Among them, one or more selected from the group consisting of m-xylylene diamine, p-xylylene diamine, 1,3-bis(aminomethyl)cyclohexane, 1,4-bis(aminomethyl)cyclohexane, and isophorone diamine are preferred, and one or more selected from the group consisting of m-xylylene diamine and isophorone diamine are more preferred.

<Polyamine Modified Product (i-1)>

As the polyamine modified product (i-1), a reaction product of the diamine represented by the formula (3) and epichlorohydrin is preferred, and those including a compound represented by the following formula (4) as a main component are more preferred, from the viewpoint of exhibiting an effect of improving a high curing rate. The "main component" as referred to herein refers to a component whose content is 50% by mass or more based on 100% by mass of the entire constituent components in the polyamine modified product (i-1).

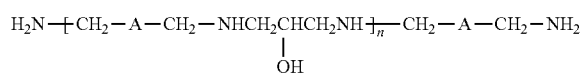

wherein A is the same as defined above. n is a number of 1 to 12.

A content of the compound represented by the formula (4) in the polyamine modified product (i-1) is preferably 60% by mass or more, more preferably 70% by mass or more, even more preferably 75% by mass or more, and still even more preferably 85% by mass or more. Further, the upper limit thereof is 100% by mass.

In addition, from the viewpoint of obtaining good curing performance as the curing agent, a compound having a high ratio of a compound with n=1 occupied in the compound represented by the formula (4) is preferred. A content of the compound with n=1 represented by the formula (4) in the polyamine modified product (i-1) is preferably 15% by mass or more, more preferably 20% by mass or more, and even more preferably 25% by mass or more.

The content of the compound represented by the formula (4) in the polyamine modified product (i-1) and the composition of the compound represented by the formula (4) may be obtained by a GC analysis and a gel permeation chromatography (GPC) analysis.

An active hydrogen equivalent weight (AHEW) of the polyamine modified product (i-1) is preferably 100 or less, more preferably 90 or less, and even more preferably 80 or less. When the AHEW of the polyamine modified product (i-1) is 100 or less, a higher curability is exhibited. The AHEW of the polyamine modified product (i-1) is preferably 45 or more, more preferably 50 or more, and even more preferably 60 or more, from the viewpoint of ease of production, and the like. The AHEW of the polyamine modified product (i-1) may be obtained by the method which is the same as defined above.

The polyamine modified product (i-1) may be obtained by subjecting a polyamine compound and epichlorohydrin to addition reaction.

The addition reaction may be performed by a well-known method, and the method is not particularly limited, but it is preferred that the addition reaction is performed in the presence of a basic catalyst from the viewpoint of reaction efficiency. As the basic catalyst, an alkali metal hydroxide is preferred, one or more selected from the group consisting of potassium hydroxide and sodium hydroxide are more preferred, and sodium hydroxide is even more preferred.

In the addition reaction of the polyamine compound and epichlorohydrin, an amount of basic catalyst used is preferably approximately equimolar to epichlorohydrin, and preferably 0.7 to 2.0 mol, more preferably 0.8 to 1.5 mol, and even more preferably 0.9 to 1.2 mol, with respect to 1 mol of epichlorohydrin used.

The amounts of polyamine compound and epichlorohydrin used in the addition reaction are not particularly limited as long as a modified product to be obtained has a ratio at which an amino group having an active hydrogen is contained, but from the viewpoint of obtaining a compound with n=1 among the compounds represented by the formula (4) at a high selectivity, a molar ratio of the polyamine compound to 1 mol of epichlorohydrin ranges preferably from 1.5 to 12 mol, more preferably from 1.5 to 6.0 mol, and even more preferably from 1.8 to 3.0 mol.

It is preferred that the addition reaction of the polyamine compound and epichlorohydrin is performed by mixing the polyamine compound and the basic catalyst in advance, and continuously adding epichlorohydrin thereto. For example, the addition reaction is performed by preparing the polyamine compound and the basic catalyst in a reactor, heating the mixture while stirring the mixture under an inert atmosphere such as a nitrogen gas, and adding epichlorohydrin thereto.

The temperature at the time of adding epichlorohydrin is preferably 40 to 100° C. and more preferably 50 to 80° C. After the addition of epichlorohydrin is completed, the reaction temperature may be increased in order to improve the reaction efficiency, and the temperature at the time of the addition reaction is preferably 55 to 120° C.

The time for the addition reaction is not particularly limited, and typically, is preferably 10 minutes to 6 hours and more preferably 20 minutes to 4 hours after the addition of epichlorohydrin is completed.

(Polyamine Modified Product (i-2))

The polyamine modified product (i-2) is a reaction product obtained by allowing the polyamine compound and a compound having at least two epoxy groups in the molecule thereof to react with each other. The preferred polyamine compound is the same as that as described above.

Specific examples of the compound (hereinafter, also referred to as "a raw material epoxy compound") having at least two epoxy groups in the molecule thereof include butyl diglycidyl ether, neopentyl glycol diglycidyl ether, 1,3-propanediol diglycidyl ether, 1,4-butanediol diglycidyl ether, 1,6-hexanediol diglycidyl ether, biphenol diglycidyl ether, dihydroxy naphthalene diglycidyl ether, dihydroxy anthracene diglycidyl ether, triglycidyl isocyanurate, tetraglycidyl glycoluril, a polyfunctional epoxy resin having a glycidyl amino group derived from metaxylylene diamine, a polyfunctional epoxy resin having a glycidyl amino group derived from 1,3-bis(aminomethyl)cyclohexane, a polyfunctional epoxy resin having a glycidyl amino group derived from diaminodiphenylmethane, a polyfunctional epoxy resin having a glycidyl amino group derived from paraaminophenol, a polyfunctional epoxy resin having a glycidyloxy group derived from paraaminophenol, a polyfunctional epoxy resin having a glycidyloxy group derived from bisphenol A, a polyfunctional epoxy resin having a glycidyloxy group derived from bisphenol F, a polyfunctional epoxy resin having a glycidyloxy group derived from phenol novolac, a polyfunctional epoxy resin having two or more glycidyloxy groups derived from resorcinol, and the like. These compounds may be used either alone or in combination of two or more thereof.

In terms of curability and performance of a cured product of an epoxy resin composition to be obtained, as a raw material epoxy compound, a compound including an aromatic ring or an alicyclic structure in the molecule thereof is more preferred, a compound including an aromatic ring in the molecule thereof is even more preferred, and a polyfunctional epoxy resin having a glycidyloxy group derived from bisphenol A is still even more preferred.

The polyamine modified product (i-2) is obtained by subjecting the polyamine compound and the compound having at least two epoxy groups in the molecule thereof (the raw material epoxy compound) to addition reaction. The addition reaction may be performed by a well-known method, and the method is not particularly limited, but examples thereof include a method of preparing a polyamine compound in a reactor, adding the raw material epoxy compound by a whole addition or a divided addition such as dropwise addition, and heating and reacting the mixture. It is preferred that the addition reaction is performed under an inert atmosphere such as a nitrogen gas.

The amounts of polyamine compound and raw material epoxy compound used in the addition reaction are not particularly limited as long as a modified product to be obtained has a ratio at which an amino group having an active hydrogen is contained, but from the viewpoint that the polyamine modified product (i-2) exhibits a function as an epoxy resin curing agent, it is preferred that in the addition reaction, an excessive amount of polyamine compound is used with respect to an epoxy equivalent weight of the raw material epoxy compound. Specifically, the raw material epoxy compound and the polyamine compound are used so as to become preferably [D]/[G]=50 to 4 and more preferably [D]/[G]=20 to 8 (here, [D] indicates the number of active hydrogens of the polyamine compound and [G] indicates the number of epoxy groups of the raw material epoxy compound). Within the range, the viscosity of the polyamine modified product (i-2) does not become excessively high, so that the handleability becomes excellent, and the performance of a cured product of an epoxy resin composition to be obtained becomes good.

The temperature and the time for the reaction at the time of the addition reaction may be appropriately selected according to the types of polyamine compound and raw material epoxy compound used, and the like. From the viewpoint of the reaction rate and the productivity, and prevention of decomposition of the raw material, and the like, the temperature at the time of the addition reaction is preferably 50 to 150° C. and more preferably 70 to 120° C. Further, the time for the reaction is preferably 0.5 to 12 hours and more preferably 1 to 6 hours after the addition of the raw material epoxy compound is completed.

<Polyamine Modified Product (ii)>

The polyamine modified product (ii) is a reaction product obtained by subjecting a polyamine compound, a phenol-based compound, and an aldehyde compound to Mannich reaction. As the polyamine compound used in the polyamine modified product (ii), one or more selected from the group consisting of the diamine represented by the formula (3) and a polyamine compound having an alicyclic structure are preferred, and one or more selected from the group consisting of o-xylylene diamine, m-xylylene diamine, p-xylylene diamine, 1,3-bis(aminomethyl)cyclohexane, 1,4-bis(aminomethyl)cyclohexane, and isophorone diamine are more preferred. Among them, one or more selected from the group consisting of m-xylylene diamine and p-xylylene diamine are preferred, and m-xylylene diamine is more preferred. In particular, the polyamine modified product (ii) using m-xylylene diamine is preferred because the curability as an epoxy resin curing agent is good, and the performance of a cured product of an epoxy resin composition to be obtained is excellent.

Examples of the phenol-based compound used in the polyamine modified product (ii) include phenol cresol, p-ethylphenol, o-isopropylphenol, p-isopropylphenol, p-tert-butylphenol, p-sec-butylphenol, o-tert-butylphenol, o-sec-butylphenol, p-tert-amylphenol, o-tert-amylphenol, p-octylphenol, nonylphenol, p-cumylphenol, decylphenol, undecylphenol, p-dodecylphenol, tridecylphenol, tetradecylphenol, pentadecylphenol, pentadecenylphenol, pentadecadienylphenol, pentadecatrienylphenol, hexadecylphenol, heptadecylphenol, octadecylphenol, octadecenylphenol, terpenephenol, and furthermore, a phenol compound naturally produced, such as cardanol. These compounds may be used either alone or in combination of two or more thereof. Among the compounds, as the phenol-based compound used in the modified product, one or more selected from the group consisting of phenol, cresol, p-tert-butylphenol, nonylphenol, and cardanol are preferred.

Examples of the aldehyde compound used in the polyamine modified product (ii) include: formaldehyde; a formaldehyde-releasing compound such as trioxane and paraformaldehyde; and other aldehydes such as benzaldehyde. Among them, one or more selected from the group consisting of formaldehyde and a formaldehyde-releasing compound are preferred. Among them, from the viewpoint of workability in the Mannich reaction, it is more preferred that an aqueous formaldehyde solution is used.

It is preferred that the polyamine modified product (ii) is a reaction product obtained by subjecting one or more polyamine compounds selected from the group consisting of the diamine represented by the formula (3) and a polyamine compound having an alicyclic structure, a phenol-based compound selected from the group consisting of phenol, cresol, p-tert-butylphenol, nonylphenol, and cardanol, and one or more aldehyde compounds selected from the group consisting of formaldehyde and a formaldehyde-releasing compound to Mannich reaction, and it is more preferred that the polyamine modified product (ii) is a reaction product obtained by subjecting one or more phenol-based compounds selected from the group consisting of m-xylylene diamine, phenol, and p-tert-butylphenol, and formaldehyde to Mannich reaction.

A method for producing the polyamine modified product (ii) is not particularly limited, and a well-known method may be used. Examples thereof include a method of adding an aldehyde compound or a solution thereof to a mixture of a polyamine compound and a phenol-based compound at preferably 80° C. or less and more preferably 60° C. or less by dropwise addition, and the like, and allowing a reaction system to react for 1 to 10 hours while removing a distillate from the reaction system by increasing the temperature to preferably 80 to 180° C. and more preferably 90 to 150° C. after the addition is completed.

The amounts of polyamine compound, phenol-based compound, and aldehyde compound used in the Mannich reaction are not particularly limited as long as a modified product to be obtained has a ratio at which an amino group having an active hydrogen is contained, but are preferably within the following range.

The aldehyde compound is used within a range of preferably 0.3 to 2 mol and more preferably 0.5 to 1.5 mol with respect to 1 mol of the polyamine compound. When the amount of aldehyde compound used with respect to 1 mol of the polyamine compound is 0.3 mol or more, the addition reaction is sufficiently performed, and when the amount thereof is 2 mol or less, the viscosity of a reaction product to be obtained does not become excessively high, so that the workability becomes good. Further, the phenol-based compound is used within a range of preferably 0.3 to 2 mol and more preferably 0.5 to 1.5 mol with respect to 1 mol of the polyamine compound. When the amount of phenol-based compound used with respect to 1 mol of the polyamine compound is 0.3 mol or more, the appearance of the cured coating film becomes good, and when the amount thereof is 2 mol or less, the curing performance as the epoxy resin curing agent is good.

When the epoxy resin curing agent of the present invention contains the other curing agent component such as a polyamine modified product, the content thereof is preferably 1% by mass or more, more preferably 5% by mass or more, even more preferably 10% by mass or more, and still even more preferably 15% by mass or more. When the content thereof is within the range, it is possible to obtain an effect of adding the other curing agent component. Further, from the viewpoint of exhibiting the performance based on the amine compound and the amine composition of the present invention, the content of the other curing agent component in the curing agent is preferably 70% by mass or less, more preferably 50% by mass or less, and even more preferably 30% by mass or less.

When the epoxy resin curing agent of the present invention contains the amine composition of the present invention and the polyamine modified product (i-1), the blending ratio of the amine composition to the polyamine modified product (i-1) in the epoxy resin curing agent is not particularly limited, and for example, the amine composition/the polyamine modified product (i-1) may be set to 1/99 to 99/1 by mass ratio. The higher the ratio of the amine composition in the epoxy resin curing agent is, the more the water resistance of a cured product of an epoxy resin composition to be obtained is improved. Meanwhile, the higher the ratio of the polyamine modified product (i-1) is, the more the curing rate is improved. From the viewpoint of improving the curing rate of the epoxy resin curing agent, and improving the water resistance of a cured product of an epoxy resin composition to be obtained, the amine composition/the polyamine modified product (i-1) is more preferably 20/80 to 95/5, and even more preferably 50/50 to 95/5, by mass ratio.

When the epoxy resin curing agent of the present invention contains the amine composition of the present invention and the polyamine modified product (i-2), the blending ratio of the amine composition to the polyamine modified product (i-2) in the epoxy resin curing agent is not particularly limited, and for example, the amine composition/the polyamine modified product (i-2) may be set to 1/99 to 99/1, 5/95 to 95/5, 10/90 to 90/10, and 20/80 to 80/20, by mass ratio. When the amine composition of the present invention is used as a main component as a curing agent component in the epoxy resin curing agent, by setting the amount of polyamine modified product (i-2) blended to 100% by mass of the total amount of the amine composition and the polyamine modified product (i-2) to, for example, 1% by mass or more, preferably 5% by mass or more, more preferably 10% by mass or more, and even more preferably 20% by mass or more, it is possible to improve the curing rate while enhancing the water resistance of a cured product of an epoxy resin composition to be obtained. Meanwhile, when the polyamine modified product (i-2) is used as a main component as a curing agent component in the epoxy resin curing agent of the present invention, by setting the amount of amine composition blended to 100% by mass of the total amount of the amine composition and the polyamine modified product (i-2) to, for example, 1% by mass or more, preferably 5% by mass or more, more preferably 10% by mass or more, and even more preferably 20% by mass or more, it is possible to obtain an effect of reducing the viscosity of the curing agent which uses the polyamine modified product (i-2) as a main component, an effect of improving the water resistance of a cured product of an epoxy resin composition to be obtained, an effect of reducing the ratio of the remaining monomer derived from the polyamine modified product (i-2) in the curing agent, and the like.

When the epoxy resin curing agent of the present invention contains the amine composition of the present invention and the polyamine modified product (ii), the blending ratio of the amine composition to the polyamine modified product (ii) in the epoxy resin curing agent is not particularly limited, and for example, the amine composition/the polyamine modified product (ii) may be set to 1/99 to 99/1, 5/95 to 95/5, 10/90 to 90/10, and 20/80 to 80/20, by mass ratio. When the amine composition of the present invention is used as a main component as a curing agent component in the epoxy resin curing agent, by setting the amount of polyamine modified product (ii) blended to 100% by mass of the total amount of the amine composition and the polyamine modified product (ii) to, for example, 1% by mass or more, preferably 5% by mass or more, more preferably 10% by mass or more, and even more preferably 20% by mass or more, it is possible to shorten the finger contact drying time or the half-drying time while enhancing the water resistance of a cured product of an epoxy resin composition to be obtained. Meanwhile, when the polyamine modified product (ii) is used as a main component as a curing agent component in the epoxy resin curing agent of the present invention, by setting the amount of the amine composition blended to 100% by mass of the total amount of the amine composition and the polyamine modified product (ii) to, for example, 1% by mass or more, preferably 5% by mass or more, more preferably 10% by mass or more, and even more preferably 20% by mass or more, it is possible to obtain an effect of reducing the viscosity of the curing agent which uses the polyamine modified product (ii) as a main component, an effect of improving the water resistance of a cured product of an epoxy resin composition to be obtained, an effect of reducing the ratio of the remaining monomer derived from the polyamine modified product (ii) in the curing agent, and the like.

Furthermore, when the epoxy resin curing agent of the present invention contains the amine composition of the present invention and the other curing agent component such as a polyamine modified product, the total content of the amine composition and the other curing agent component in the epoxy resin curing agent is preferably 50% by mass or more, more preferably 70% by mass or more, and even more preferably 80% by mass or more, from the viewpoint of the curability as the epoxy resin curing agent and obtaining an epoxy resin composition capable of providing a cured product having good properties. Further, the upper limit thereof is 100% by mass.

A well-known curing accelerator, a non-reactive diluent, or the like may also be blended with the epoxy resin curing agent of the present invention, within a range not impairing the effects of the present invention. When the epoxy resin curing agent of the present invention also contains a curing accelerator, the epoxy resin curing agent is preferred from the viewpoint of improving the curing rate.

As the curing accelerator, an organic compound having one or more functional groups selected from the group consisting of an amino group, a hydroxyl group, and a carboxy group is preferred. Examples thereof include: an organic compound having an amino group, such as dimethylethylamine and triethylamine; an organic compound having a hydroxyl group, such as phenol, benzyl alcohol, styrenated phenol, and bisphenol A; an organic compound having a carboxy group, such as formic acid, acetic acid, propionic acid, and butyric acid; an organic compound having an amino group and a hydroxy group, such as aminoethanol, 2-dimethylaminomethyl phenol, and 2,4,6-tris(dimethylaminomethyl)phenol; and an organic compound having a hydroxy group and a carboxy group, such as lactic acid, malic acid, tartaric acid, salicylic acid, dihydroxy benzoic acid, trihydroxybenzoic acid, 2-hydroxy-3-isopropyl benzoic acid, hydroxynaphthoic acid, dihydroxynaphthoic acid, and hydroxy methoxy naphthoic acid. These curing accelerators may be used either alone or in combination of two or more thereof. Further, the number of carbon atoms of the curing accelerator ranges preferably from 2 to 50, more preferably from 2 to 40, and even more preferably from 6 to 30, from the viewpoint of the solubility in the epoxy resin curing agent, and an effect of accelerating the curing.

Among them, as the curing accelerator, an organic compound at least having a hydroxy group is preferred, one or more selected from the group consisting of an organic compound having a hydroxy group and an organic compound having a hydroxy group and a carboxy group are more preferred, and from the viewpoint of the solubility in the epoxy resin curing agent, and an effect of accelerating the curing, one or more selected from the group consisting of styrenated phenol and salicylic acid are even more preferred.

The styrenated phenol is a compound represented by the following structural formula, and m in the following formula is 1 to 5, preferably 1 to 3. The styrenated phenol may be a mixture of compounds of which the numbers of m in the following structural formula are different.

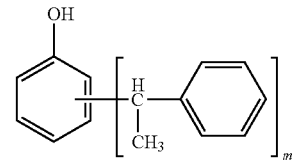

[Chem. 7]

The content of the curing accelerator in the epoxy resin curing agent is preferably 1% by mass or more, more preferably 2% by mass or more, and even more preferably 3% by mass or more, from the viewpoint of obtaining an effect of accelerating the curing. Further, from the viewpoint of enhancing the performance of a cured product of an epoxy resin composition to be obtained, the content thereof is preferably 30% by mass or less and more preferably 20% by mass or less.

An active hydrogen equivalent weight (AHEW) of the epoxy resin curing agent of the present invention is preferably 130 or less, more preferably 120 or less, and even more preferably 110 or less. When the AHEW of the curing agent is 130 or less, high curability is exhibited even though the amount of curing agent blended to the epoxy resin composition is small. Meanwhile, from the viewpoint of the water resistance of a cured coating film of an epoxy resin composition to be obtained and obtaining an excellent appearance thereof, the AHEW of the curing agent is preferably 60 or more and more preferably 65 or more.

<Curing Agent for Water-Based Epoxy Resin>

The epoxy resin curing agent of the present invention may also be used as a curing agent for a water-based epoxy resin. The "water-based epoxy resin" in the present specification refers to an aqueous epoxy resin, or an epoxy resin used in an aqueous dispersion state. The water-based epoxy resin will be described below, but as the water-based epoxy resin used in the present invention, an epoxy resin emulsion is preferred.

The curing agent for a water-based epoxy resin is not particularly limited as long as the curing agent contains the amine compound of the present invention or the amine composition of the present invention, which is described above, and for example, a curing agent which is the same as the above-described epoxy resin curing agent may be used.

Among them, the content of the amine composition in the curing agent for a water-based epoxy resin is preferably 30% by mass or more, more preferably 50% by mass or more, even more preferably 70% by mass or more, and still even more preferably 85% by mass or more. Further, the upper limit thereof is 100% by mass. When the content of the amine composition in the curing agent for a water-based epoxy resin is 30% by mass or more, the water resistance, the appearance, and the hardness of a cured coating film of a water-based epoxy resin composition using the curing agent are enhanced.

[Epoxy Resin Composition]

The epoxy resin composition of the present invention contains the above-described epoxy resin curing agent of the present invention and an epoxy resin. The epoxy resin composition of the present invention may be any one of a non-water-based epoxy resin composition and a water-based epoxy resin composition. In the following description, unless otherwise specifically mentioned, the non-water-based epoxy resin composition and the water-based epoxy resin composition are collectively defined as "the epoxy resin composition of the present invention."

In the present specification, the "non-water-based epoxy resin composition" is an epoxy resin composition in which the content of water in the epoxy resin composition is less than 10% by mass, preferably less than 5% by mass, and more preferably less than 2% by mass. From the viewpoint of the performance of a cured product of an epoxy resin composition to be obtained, it is preferred that the epoxy resin composition of the present invention is a non-water-based epoxy resin composition.

In the present specification, the "water-based epoxy resin composition" is an epoxy resin composition in which the content of water in the epoxy resin composition is 10% by mass or more, preferably 15% by mass or more, and more preferably 20% by mass or more. The upper limit of the content of water may be appropriately adjusted according to the concentration of the water-based epoxy resin composition, but is typically 80% by mass or less, and preferably 60% by mass or less.

Further, it is preferred that the water-based epoxy resin composition does not include an organic solvent, and the content thereof is preferably 10% by mass or less, more preferably 5% by mass or less, and even more preferably 2% by mass or less.

As the epoxy resin used in the non-water-based epoxy resin composition, any epoxy resin may be used as long as the epoxy resin is an epoxy resin having a glycidyl group which reacts with an active hydrogen of the epoxy resin curing agent of the present invention, but from the viewpoint that the performance of a cured product is excellent, an epoxy resin including an aromatic ring or an alicyclic structure in the molecule thereof is preferred.

Specific examples of the epoxy resin include one or more resins selected from the group consisting of an epoxy resin having a glycidylamino group derived from metaxylylene diamine, an epoxy resin having a glycidylamino group derived from 1,3-bis(aminomethyl)cyclohexane, an epoxy resin having a glycidylamino group derived from diaminodiphenylmethane, an epoxy resin having a glycidylamino group derived from paraaminophenol, an epoxy resin having a glycidyloxy group derived from paraaminophenol, an epoxy resin having a glycidyloxy group derived from bisphenol A, an epoxy resin having a glycidyloxy group derived from bisphenol F, an epoxy resin having a glycidyloxy group derived from phenol novolac, and an epoxy resin having a glycidyloxy group derived from resorcinol. In order to improve various performances such as flexibility, impact resistance, and wet heat resistance, two or more of the various epoxy resins may be mixed and used.

Among them, from the viewpoint of the performance of a cured product, it is more preferred that the epoxy resin includes, as a main component, one or more selected from the group consisting of an epoxy resin having a glycidylamino group derived from metaxylylene diamine, an epoxy resin having a glycidyloxy group derived from bisphenol A, and an epoxy resin having a glycidyloxy group derived from bisphenol F, and it is even more preferred that the epoxy resin includes, as a main component, one or more selected from the group consisting of an epoxy resin having a glycidyloxy group derived from bisphenol A and an epoxy resin having a glycidyloxy group derived from bisphenol F.

Further, the "main component" means that other components may be included without departing from the gist of the present invention, and means preferably 50 to 100% by mass, more preferably 70 to 100% by mass, and even more preferably 90 to 100% by mass of the total components.

As the water-based epoxy resin used in the water-based epoxy resin composition, an epoxy resin emulsion is preferred as described above.

Examples of the epoxy resin emulsion include an epoxy resin emulsion in which an epoxy resin is emulsified and dispersed in water. As the epoxy resin, both a self-emulsifiable epoxy resin and a non-self-emulsifiable epoxy resin may be used.

When the non-self-emulsifiable epoxy resin is used, for example, an epoxy resin emulsion may be formulated by dispersing a non-self-emulsifiable epoxy resin in water in the presence of an emulsifier. The emulsifier may be any one of an anionic emulsifier, a nonionic emulsifier, and a cationic emulsifier, but the nonionic emulsifier is preferred in that the selection range of the curing agent is wide.

As the epoxy resin used in the epoxy resin emulsion, any epoxy resin may be used as long as the epoxy resin is an epoxy resin which has a glycidyl group reacting with an active hydrogen of the epoxy resin curing agent of the present invention, and may also be emulsified and dispersed in water. From the viewpoint of the water resistance or the hardness of a cured coating film of a water-based epoxy resin composition, an epoxy resin including an aromatic ring or an alicyclic structure in the molecule thereof is preferred.

Specific examples of the epoxy resin used in the epoxy resin emulsion include one or more resins selected from the group consisting of an epoxy resin having a glycidylamino group derived from metaxylylene diamine, an epoxy resin having a glycidylamino group derived from 1,3-bis(aminomethyl)cyclohexane, an epoxy resin having a glycidylamino group derived from diaminodiphenylmethane, an epoxy resin having a glycidylamino group derived from paraaminophenol, an epoxy resin having a glycidyloxy group derived from paraaminophenol, an epoxy resin having a glycidyloxy group derived from bisphenol A, an epoxy resin having a glycidyloxy group derived from bisphenol F, an epoxy resin having a glycidyloxy group derived from phenol novolac, and an epoxy resin having a glycidyloxy group derived from resorcinol.

Among them, from the viewpoint of the water resistance or the hardness of the cured coating film of the water-based epoxy resin composition, it is more preferred that the epoxy resin used in the epoxy resin emulsion includes, as a main component, one or more selected from the group consisting of an epoxy resin having a glycidylamino group derived from metaxylylene diamine, an epoxy resin having a glycidyloxy group derived from bisphenol A, and an epoxy resin having a glycidyloxy group derived from bisphenol F, it is even more preferred that the epoxy resin used in the epoxy resin emulsion includes, as a main component, one or more selected from the group consisting of an epoxy resin having a glycidyloxy group derived from bisphenol A and an epoxy resin having a glycidyloxy group derived from bisphenol F, and it is still even more preferred that the epoxy resin used in the epoxy resin emulsion includes, as a main component, an epoxy resin having a glycidyloxy group derived from bisphenol A.

An epoxy equivalent weight of an epoxy resin used in an epoxy resin emulsion is preferably 150 g/equivalent weight or more, more preferably 200 g/equivalent weight or more, even more preferably 300 g/equivalent weight or more, and still even more preferably 500 g/equivalent weight or more, from the viewpoint of the water resistance or the hardness of a cured coating film of a water-based epoxy resin composition to be obtained, and is preferably 1,000 g/equivalent weight or less and more preferably 800 g/equivalent weight or less, from the viewpoint of the low viscosity or the curability of the water-based epoxy resin composition.

In the case of an epoxy resin emulsion in which an epoxy resin is dispersed in water in the presence of an emulsifier, it is preferred that an epoxy equivalent weight of a component (solid content) in which a dispersion medium is removed from the emulsion is also within the range.

The epoxy resins used in the epoxy resin emulsion may be used alone and may be used in combination of two or more thereof.

Further, an epoxy equivalent weight in an epoxy resin emulsion state is preferably 150 g/equivalent weight or more, more preferably 200 g/equivalent weight or more, even more preferably 300 g/equivalent weight or more, and still even more preferably 500 g/equivalent weight or more, from the viewpoint of the water resistance or the hardness of a cured coating film of a water-based epoxy resin composition to be obtained, and is preferably 1,500 g/equivalent weight or less from the viewpoint of the low viscosity or the curability of the water-based epoxy resin composition.

The concentration of the epoxy resin in the epoxy resin emulsion is not particularly limited, but is preferably 40% by mass or more and more preferably 50% by mass or more, and typically 80% by mass or less.

Examples of an epoxy resin emulsion which may be used as a water-based epoxy resin include commercially available products, such as "W2801," "W2821R70," "W3435R67," "W8735R70," "W1155R55," and "W5654R45," which are jER series manufactured by Mitsubishi Chemical Corporation, "EM-101-50" manufactured by ADEKA Corporation, "EPICLONEXA-8610" manufactured by DIC Corporation, "PZ 3901," "PZ 3921," and "PZ 3961-1," which are Araldite series manufactured by Huntsman Advanced Materials, Inc., "DER915" and "DER917" manufactured by Olin Corporation, and "Resin 3520-WY-55" and "Resin 6520-WH-53," which are EPIREZ series manufactured by Hexion Specialty Chemicals.

The content of the epoxy resin curing agent in the epoxy resin composition of the present invention is an amount in which the ratio of the number of active hydrogens in the epoxy resin curing agent to the number of epoxy groups in the epoxy resin is preferably 1/0.8 to 1/1.2, more preferably 1/0.9 to 1/1.1, and even more preferably 1/1.

In the epoxy resin composition of the present invention, a modifying component such as a filler and a plasticizer, a flow control component such as a thixotropic agent, and other components such as a pigment, a leveling agent, a tackifier may also be contained according to the use.

A preparation method of the epoxy resin composition of the present invention is not particularly limited, and an epoxy resin curing agent, an epoxy resin, and other components, if necessary, may be mixed and produced by using well-known methods and apparatuses.

[Paint, Adhesive, Floor Material, and Sealant]

The present invention also provides a paint, an adhesive, a flooring material, and a sealant, which contain the epoxy resin composition of the present invention. Examples of the paint include a paint for corrosion resistance. The epoxy resin composition of the present invention provides good performance of a cured product and is also excellent in water resistance or chemical resistance. For this reason, the epoxy resin composition is suitably used for various paints such as a paint for corrosion resistance, an adhesive, a floor material, a sealant, and the like.

[Cured Product of Epoxy Resin Composition]

A cured product of the epoxy resin composition of the present invention (hereinafter, also simply referred to as "the cured product of the present invention") is a cured product obtained by curing the above-described epoxy resin composition of the present invention by a well-known method. The curing conditions of the epoxy resin composition are appropriately selected according to the use and the form, and are not particularly limited.

The form of the cured product of the present invention is also not particularly limited, and may be selected according to the use. For example, when the epoxy resin composition is used for various paints, the cured product is usually a film-like cured product. When the cured product is a floor material, the cured product is usually a film-like cured product, and when the cured product is a sealant, the cured product is usually a sheet-like cured product. When the cured product of the present invention is a film-like or sheet-like cured product, the cured product is preferred in that the good performance of the cured product may be exhibited.

When the cured product of the present invention is a film-like or sheet-like cured product, the thickness thereof is not particularly limited, and may be selected according to the use within a range of, for example, 0.5 µm to 5 mm.

EXAMPLES

Hereinafter, the present invention will be described in detail with reference to Examples and Comparative Examples, but the present invention is not limited to the following Examples. Further, the amine compound and the amine composition were analyzed and evaluated by the following methods.

(Gas Chromatography (GC) Analysis)

The styrene reaction rate and the content ratio of each component in the amine composition were measured under the following conditions by a GC analysis.

Apparatus; "7890B GC" manufactured by Agilent Technologies, Inc.

Column; "CP-Sil 8 CB for Amines" (length 30 m, film thickness 0.25 µm, and inner diameter 0.25 mm) manufactured by Agilent Technologies, Inc.

Column temperature; 150° C. 2 minutes→10° C./min temperature increase →300° C. 60 minutes
Carrier gas: Helium
Carrier gas flow rate: 1.36 mL/min
Inlet pressure: 33.473 psi (constant pressure mode)
Detector: FID
Inlet temperature: 300° C.
Detector temperature: 300° C.

(Ultra High Performance Liquid Chromatography (UHPLC) Analysis)

The obtained amine composition was purified by UHPLC fractionation under the following conditions to isolate a 1:1 adduct of MXDA and styrene.

Liquid chromatography apparatus; "UltiMate3000RS system" manufactured by Thermo Fisher Scientific, Inc.
Column; "BEH C18" (length 50 mm, inner diameter 2.1 mm, and particle size 1.7 μm) manufactured by Waters Co., Ltd.
Column oven temperature; 40° C.
Detector; UV
Detection wavelength; 210 nm
Injection amount; 0.3 μL By using Carrier; A: ultrapure water, B: acetonitrile, C: an aqueous 50 mM trifluoroacetic acid solution, the ratio was changed in a gradient mode from measurement 0 minute (A:B:C=80:10:10 (vol %)) to after 18 minutes (A:B:C=0:90:10 (vol %)).
Carrier flow rate; 0.3 mL/min (Gas Chromatograph Mass Spectrometry (GC-MS))

Structure identification by mass spectrometry of each component included in the obtained amine compound and amine composition was carried out under the following conditions by gas chromatograph mass spectrometry (GC-MS).

<Analysis Condition (EI+ Mode)>
Apparatus; "7890N GC" manufactured by Agilent Technologies, Inc.
Column; "DB-1MS" (length 30 m, film thickness 0.25 μm, and inner diameter 0.25 mm) manufactured by Agilent Technologies, Inc.
Carrier gas; Helium
Carrier gas flow rate; 1.0 mL/min
Oven program; 50° C. for 5 minutes→20° C./min temperature increase→320° C. for 10 minutes
Injection amount; 1 μL
Injection mode; Split mode
Split ratio; 1:100
Inlet temperature; 300° C.
Mass spectrometer; "AccuTOF GCv 4G" manufactured by JEOL Ltd.
Mass range; m/z=33 to 700
Interface temperature; 300° C.
Ionization method; Electron ionization method (EI+)
Ionization energy; 70 eV
Ion source temperature; 250° C.

<Analysis Condition (FI+ Mode)>
Apparatus; "7890N GC" manufactured by Agilent Technologies, Inc.
Column; "DB-1MS" (length 30 m, film thickness 0.25 μm, and inner diameter 0.25 mm) manufactured by Agilent Technologies, Inc.
Carrier gas; Helium
Carrier gas flow rate; 1.0 mL/min
Oven program; 50° C. for 5 minutes→20° C./min temperature increase→320° C. for 10 minutes
Injection amount; 1 μL
Injection mode; Split mode
Split ratio; 1:50
Inlet temperature; 300° C.
Mass spectrometer; "AccuTOF GCv 4G" manufactured by JEOL Ltd.
Mass range; m/z=33 to 700
Interface temperature; 300° C.
Ionization method; Field ionization method (FI+)
Ion source temperature; 60° C.
Emitter current; 0 mA ($^1$H-NMR, $^{13}$C-NMR Analysis)

Structure identification of each component included in the obtained amine compound and amine composition was carried out under the following conditions by $^1$H-NMR and $^{13}$C-NMR.

Nuclear magnetic resonance spectrometer; AVANCE 3-500 manufactured by Bruker
Probe; 5 mmcp double resonance polynucleotide probe (BBFO probe)
Heavy solvent; Heavy methanol
Measurement nucleus; 1H, 13C
Measurement temperature; Room temperature (Measurement of Active Hydrogen Equivalent Weight (AHEW))

The active hydrogen equivalent weight (AHEW) of the amine composition was measured by the titration method described below.

The total amine value and the secondary and tertiary amine values of the amine composition were each measured using an automatic potentiometric titration apparatus "AT-610" (manufactured by Kyoto Electronics Industry Co., Ltd.). The total amine value was measured by performing a potentiometric titration with a 0.1 mol/L perchloric acid-acetic acid solution (manufactured by Kanto Chemical Co., Ltd.). The secondary and tertiary amine values were measured by dissolving a sample in isopropanol (manufactured by Kanto Chemical Co., Ltd.), adding salicylaldehyde, allowing the resulting mixture to stand for 30 minutes, and then performing a potentiometric titration with 0.1 mol/11 of 2-propanolic hydrochloric acid (manufactured by Wako Pure Chemical Industries, Ltd.). The AHEW was calculated from these results.

However, with respect to the AHEW of each of the amine compositions obtained in Examples A-4 to A-6, A-10, and A-11, the content ratio of each component in the amine composition was obtained by the GC analysis, and from the results, the AHEW of the amine composition was calculated.

(Measurement of Viscosity)

The viscosity of the amine composition at 25° C. was measured by means of an E-type viscometer "TVE-22H type viscometer cone plate type" (manufactured by Toki Sangyo Co., Ltd.).

(Measurement of Gardener Color Scale)

The Gardner color scale of the amine composition was measured according to a method in accordance with JIS K0071-2 by means of an instrument of simultaneously measuring a color and a turbidity "COH400" (manufactured by Nippon Denshoku Industries Co., Ltd.).

Examples A-1 to A-13, Comparative Example A-1:
Preparation of Amine Compound and Amine Composition Example A-1

A 1 liter four-necked separable flask was equipped with a stirrer, an Aerene type cooler, a thermocouple, and a nitrogen introduction tube, and after the flask was purged with nitrogen, 408.6 g (3.0 mol) of metaxylylene diamine (MXDA, manufactured by Mitsubishi Gas Chemical Company, Inc.), which is a raw material diamine, was added thereto. Next, 4.9 g of sodium amide (manufactured by Wako Pure Chemical Industries, Ltd.) and 14.0 g of potassium t-butoxide (manufactured by Tokyo Chemical Industry Co., Ltd.), which are alkali metal-containing catalysts, were weighed in a polyethylene bottle in a simple glove box, and added quickly to the flask. When the total amount of MXDA and styrene used was taken as 100% by mass (100 mol %), the catalyst amounts were 0.68% by mass (2.1 mol %) of $NaNH_2$ and 1.95% by mass (2.1 mol %) of potassium t-butoxide, respectively. While stirring the inside of the flask, the flask was heated with a mantle heater such that the solution temperature was 80° C., and 10 minutes after the temperature reached 80° C., it was confirmed visually that the liquid color in the flask was changed from colorless to dark purple. After the liquid color was changed to dark purple, the flask was heated at 80° C. for 40 minutes.

After heating, the nitrogen inlet tube was removed, and a dropping funnel was mounted. While heating and stirring were continued, 312.5 g (3.0 mol) of styrene was dropped from the dropping funnel over 2 hours, and after the completion of dropwise addition, metaxylylene diamine and styrene, the resulting mixture was stirred under heating at 80° C. for 30 minutes to react with each other. After stopping the reaction by adding water to the reaction solution, 25 g of Celite 503 (manufactured by Kanto Chemical Co., Ltd.) was added to this solution, and the resulting mixture was stirred at 75 to 80° C. for 1 hour. After stirring, the mixture was cooled to room temperature and then filtered through a glass filter to obtain a crude product. The styrene reaction rate was 100%.

Next, the crude product was transferred to a 1 L 4-neck round bottom flask, the flask was equipped with a magnet drive vacuum stirrer, a thermocouple, and a Liebig condenser, and the product was dehydrated under conditions of a temperature of 60° C. and a pressure of 90 hPa. After the distillation of water stopped, the pressure was reduced to 1 hPa or less, and the unreacted raw material metaxylylene diamine was distilled off at 140° C. After cooling, Celite 503 (manufactured by Kanto Chemical Co., Ltd.) was added to the solution, and the mixture was stirred, and then filtered through a glass filter to obtain an amine composition A including an adduct of metaxylylene diamine and styrene.

The obtained amine composition A was purified by UHPLC fractionation under the above-mentioned conditions, and a compound exhibiting a peak detected at a retention time (RT) of 4.35 minutes in the UHPLC analysis was isolated. As a result of carrying out a structural analysis by the GC-MS analysis, the $^1$H-NMR analysis, and the $^{13}$C-NMR analysis, it was found that the compound was an amine compound (hereinafter, also referred to as "compound (1-1)") represented by the following structural formula (1-1), which is a 1:1 adduct of MXDA and styrene.

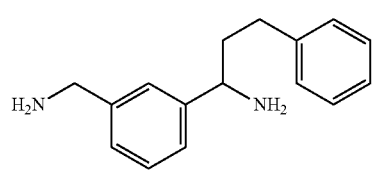

(1-1)

FIG. 1 is a chart of a mass spectrum of the compound (1-1) when the GC-MS analysis is carried out on the EI+ mode. In the chart of FIG. 1, the peak at m/z=135 was determined as a peak of MXDA generated by a fragment.

Figure 2:
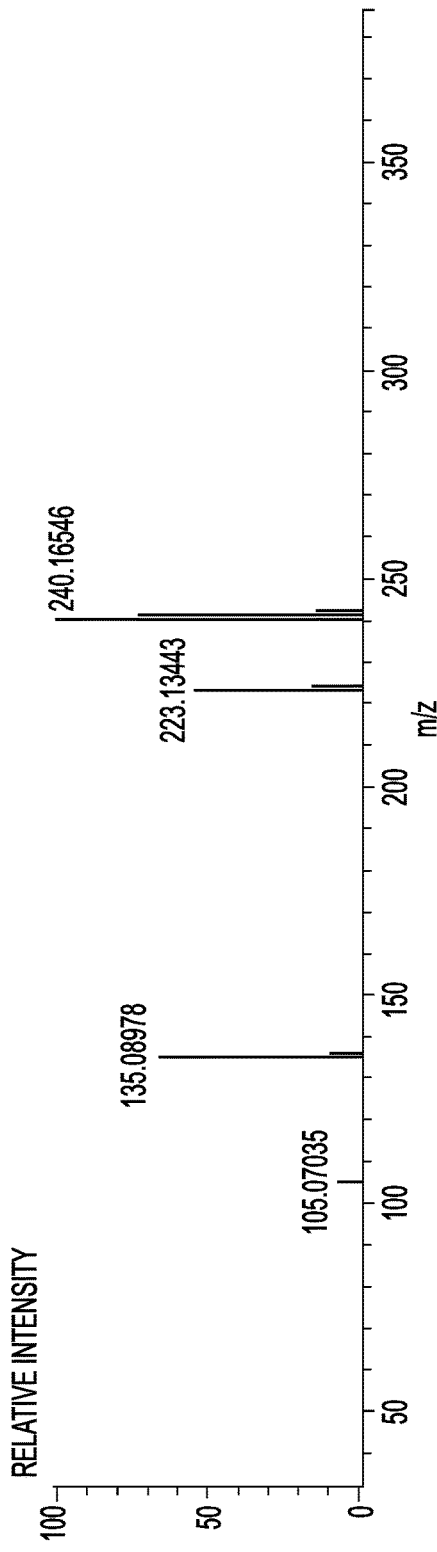
FIG. 2 is a chart of a mass spectrum when a GC-MS analysis is carried out on the compound (1-1) on the FI+ mode.

Further, FIG. 2 is a chart of a mass spectrum of the compound (1-1) when the GC-MS analysis is carried out on the FI+ mode, and the peak at m/z=240 was determined as a peak of a 1:1 adduct of MXDA and styrene.

FIG. 3 is a $^1$H-NMR spectrum of the compound (1-1). δ1.98-2.11 ppm (m, 2H, the following 2), δ2.46-2.60 ppm (m, 2H, the following 1), 3.84 ppm (s, 2H, the following 4), 3.85-3.88 ppm (dd, 1H, the following 3), 7.13-7.36 ppm (m, 13H, —N$\underline{H}_2$×2, $C_6\underline{H}_5$, $C_6\underline{H}_4$)

[Chem. 9]

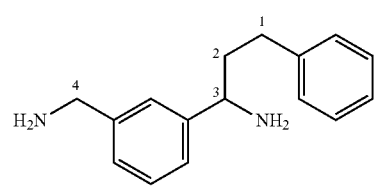

FIG. 4 is a 13C-NMR spectrum of the compound (1-1). δ33.7 ppm (the following 1), 41.6 ppm (the following 2), 46.4 ppm (the following 4), 56.8 ppm (the following 3), 126.7, 126.9, 127.0, 127.7, 129.4, 129.4, 130.0, 142.9, 143.1 ppm (a phenyl group (C6), and carbon (C5) of a phenylene group except for the following 5), 146.4 ppm (the following 5)

[Chem. 10]

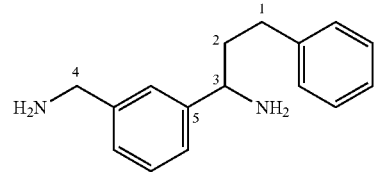

Further, as a result of the GC analysis of the amine composition A, the content of the compound represented by the structural formula (1-1) in the amine composition A was 38.2% by mass. The amine composition A is also represented by the following structural formula (2-1), and the amine composition A includes an amine compound which is a 1:1 adduct of MXDA and styrene, and the content (hereinafter, expressed as "[(1)/(1)+(2)]") of the amine compound represented by the structural formula (1-1) was 67% by mass based on 100% by mass of the total amount of the amine compound represented by the structural formula (1-1) and the amine compound represented by the structural formula (2-1) in the amine composition A, and a content ratio (in Table 1, expressed as "a 1/2/3 adduct ratio") of a 1:1 adduct of MXDA and styrene, a 1:2 adduct of MXDA and styrene, and a 1:3 adduct of MXDA and styrene was 57/36/7 as the peak area ratio of GC analysis. Further, the amine composition A had an AHEW of 81 and a viscosity of 218 mPa·s at a temperature of 25° C. The analysis results are shown in Table 1.

(2-1)

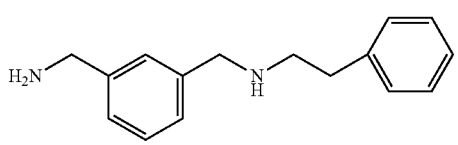

In addition, in the GC analysis, the retention time (RT) of each of the peaks corresponding to a 1:1 adduct, a 1:2 adduct, and a 1:3 adduct of MXDA and styrene was as follows.

1:1 Adduct (the structural formula (2-1)): 13.5 minutes

1:1 Adduct (the structural formula (1-1)): 13.7 minutes

1:2 Adduct (the following structural formula A): 19.8 minutes

1:2 Adduct (the following structural formula B): 20.1 minutes

1:2 Adduct (the following structural formula C): 21.5 minutes

1:2 Adduct (the following structural formula D): 21.7 minutes

1:2 Adduct (the following structural formula E): 21.9 minutes

1:3 Adduct: 38.5 to 40.5 minutes (A)

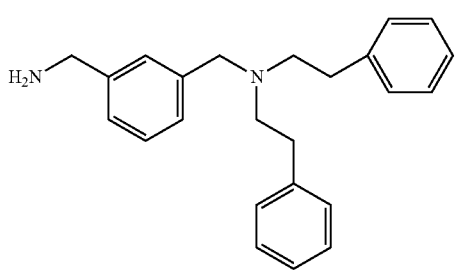

(B)

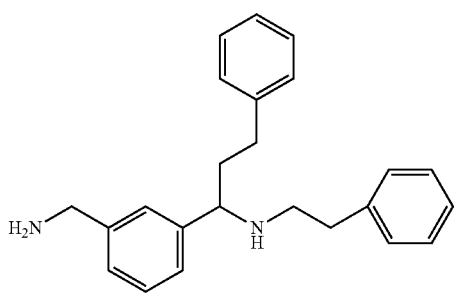

(C)

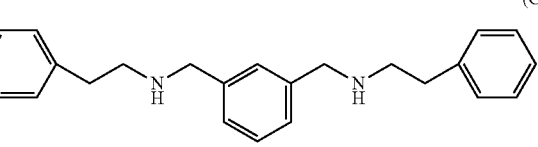

(D)

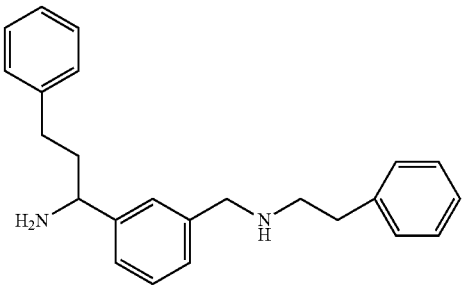

(E)

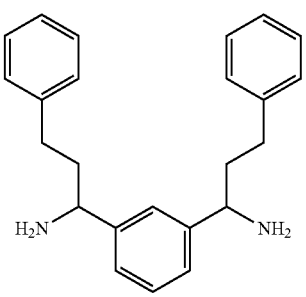

Examples A-2 to A-4

Amine Compositions B to D were produced in the same manner as in Example A-1, except that in Example A-1, the amounts of alkali metal-containing catalysts used were changed as shown in Table 1. The analysis results are shown in Table 1.

Example A-5

Amine Composition E was produced in the same manner as in Example A-2, except that in Example A-2, 13.8 g (0.185 mol) of potassium chloride (manufactured by Kanto Chemical Co., Ltd.) was used instead of potassium t-butoxide among the alkali metal-containing catalysts used. The analysis results are shown in Table 1.

Example A-6

Amine Composition F was produced in the same manner as in Example A-5, except that in Example A-5, the amounts of alkali metal-containing catalysts used were changed as shown in Table 1. The analysis results are shown in Table 1.

Example A-7

Amine Composition G was produced in the same manner as in Example A-2, except that in Example A-2, 10.4 g (0.185 mol) of potassium hydroxide (manufactured by Kanto Chemical Co., Ltd.) was used instead of potassium t-butoxide among the alkali metal-containing catalysts used. The analysis results are shown in Table 1.

Example A-8

Amine composition H was produced by mixing a commercially available adduct of metaxylylene diamine and styrene ("GASKAMINE240," AHEW 103, manufactured by Mitsubishi Gas Chemical Company, Inc.) with the amine composition A obtained in Example A-1 so as to become the composition ratios shown in Table 1. The results are shown in Table 1.

Example A-9

Amine Composition I was produced in the same manner as in Example A-1, except that in Example A-1, the alkali metal-containing catalysts used were changed into 1.4 g (0.061 mol) of lithium amide (manufactured by Kanto Chemical Co., Ltd.) and 7.0 g (0.062 mol) of potassium t-butoxide (manufactured by Tokyo Chemical Industry Co., Ltd.). The analysis results are shown in Table 1.

Examples A-10 and A-11

Amine Compositions J and K were produced in the same manner as in Example A-1, except that in Example A-1, the amounts of alkali metal-containing catalysts used and the reaction temperature were changed as shown in Table 1. The analysis results are shown in Table 1.

Example A-12

Amine Composition L was produced in the same manner as in Example A-1, except that in Example A-1, the amounts of alkali metal-containing catalysts used were changed as shown in Table 1. The analysis results are shown in Table 1.

Example A-13

In Example A-12, Amine Composition M was produced by adding the alkali metal-containing catalyst two times dividedly. The specific procedure is as follows.

A 1 liter four-necked separable flask was equipped with a stirrer, an Aerene type cooler, a thermocouple, and a nitrogen introduction tube, and after the flask was purged with nitrogen, 408.6 g (3.0 mol) of metaxylylene diamine (MXDA, manufactured by Mitsubishi Gas Chemical Company, Inc.), which is a raw material diamine, was added thereto. Next, 1.8 g of sodium amide (manufactured by Wako Pure Chemical Industries, Ltd.) and 2.6 g of potassium t-butoxide (manufactured by Tokyo Chemical Industry Co., Ltd.), which are alkali metal-containing catalysts, were weighed in a polyethylene bottle in a simple glove box, and added quickly to the flask. While stirring the inside of the flask, the flask was heated with a mantle heater such that the solution temperature was 80° C., and 10 minutes after the temperature reached 80° C., it was confirmed visually that the liquid color in the flask was changed from colorless to dark purple. After the liquid color was changed to dark purple, the flask was heated at 80° C. for 40 minutes.

After heating, the nitrogen inlet tube was removed, and a dropping funnel was mounted. 156.25 g (1.5 mol) of styrene was dropped from the dropping funnel over 1 hour while heating and stirring were continued, and after the completion of dropwise addition, 1.8 g of sodium amide and 2.6 g of potassium t-butoxide, which are alkali metal-containing catalysts, were weighed in a polyethylene bottle in a simple glove box and quickly added to the flask. When the total amount of MXDA and styrene used was taken as 100% by mass (100 mol %), the total amounts of catalysts were 0.5% by mass (1.5 mol %) of $NaNH_2$ and 0.72% by mass (0.77 mol %) of potassium t-butoxide, respectively. Thereafter, 156.25 g (1.5 mol) of styrene was dropped from the dropping funnel over 1 hour while heating and stirring were continued again. After the completion of dropwise addition, metaxylylene diamine and styrene were allowed to react with each other by stirring the mixture under heating at 80° C. for 30 minutes. After stopping the reaction by adding water to the reaction solution, 25 g of Celite 503 (manufactured by Kanto Chemical Co., Ltd.) was added to this solution, and the resulting mixture was stirred at 75 to 80° C. for 1 hour. After stirring, the mixture was cooled to room temperature and then filtered through a glass filter to obtain a crude product. The styrene reaction rate was 100%.

Next, the crude product was transferred to a 1 L 4-neck round bottom flask, the flask was equipped with a magnet drive vacuum stirrer, a thermocouple, and a Liebig condenser, and the product was dehydrated under conditions of a temperature of 60° C. and a pressure of 90 hPa. After the distillation of water stopped, the pressure was reduced to 1 hPa or less, and the unreacted raw material metaxylylene diamine was distilled off at 140° C. After cooling, Celite 503 (manufactured by Kanto Chemical Co., Ltd.) was added to the solution, and the mixture was stirred and then filtered through a glass filter to obtain an amine composition M including an adduct of metaxylylene diamine and styrene.

The analysis results of Amine Composition M are shown in Table 1.

Further, when the results of Example A-12 and Example A-13 were compared with each other, the styrene reaction rate in Example A-13 in which the catalyst was added dividedly was higher than that in Example A-12. In addition, it was found that Amine Composition M obtained in Example A-13 had a lower Gardner color scale value and a less-colored amine composition might be obtained.

Comparative Example A-1

The production of an adduct with styrene was tested by using 1,3-bis(aminomethyl)cyclohexane instead of MXDA as a raw material diamine.

A 2 liter four-necked separable flask was equipped with a stirrer, an Aerene type cooler, a thermocouple, and a nitrogen introduction tube, and after the flask was purged with nitrogen, 426.6 g (3.0 mol) of 1,3-bis(aminomethyl)cyclohexane (1,3-BAC, manufactured by Mitsubishi Gas Chemical Company, Inc.) was added thereto. Next, 7.2 g (0.31 mol) of sodium amide (manufactured by Wako Pure Chemical Industries, Ltd.) and 10.86 g (0.097 mol) of potassium t-butoxide (manufactured by Tokyo Chemical Industry Co., Ltd.), which are alkali metal-containing catalysts, were weighed in a polyethylene bottle in a simple glove box, and added quickly to the flask. When the total sum of 1,3-BAC and styrene used was taken as 100% by mass (100 mol %), the catalyst amounts were 1.0% by mass (3.1 mol %) of $NaNH_2$ and 1.5% by mass (1.6 mol %) of potassium t-butoxide, respectively. While stirring the inside of the flask, the flask was heated with a mantle heater such that the solution temperature was 100° C., and the mixture was heated and stirred for 120 minutes. On the way, it was confirmed visually that the liquid color in the flask was changed from colorless to reddish purple.

After heating, the nitrogen inlet tube was removed, and a dropping funnel was mounted. While heating and stirring were continued, 312.5 g (3.0 mol) of styrene was dropped from the dropping funnel over 2 hours, and after the completion of dropwise addition, 1,3-BAC and styrene were allowed to react with each other by stirring the resulting mixture under heating at 100° C. for 30 minutes. After stopping the reaction by adding water to the reaction solution, 25 g of Celite 503 was added to this solution, and the resulting mixture was stirred at 75 to 80° C. for 1 hour. After stirring, the mixture was cooled to room temperature and then filtered through a glass filter to obtain a crude product. The styrene reaction rate was 43%.

However, as a result of the GC analysis of the crude product, a product in which the active hydrogen of the amino group of 1,3-BAC was substituted with styrene was obtained, but a product having a structure in which the hydrogen of the methylene of the aminomethyl group of 1,3-BAC was substituted with styrene was not obtained.

TABLE 1

| | | Example | | | | | | |
|---|---|---|---|---|---|---|---|---|
| | | A-1 | A-2 | A-3 | A-4 | A-5 | A-6 | A-7 |
| Production conditions | Diamine | MXDA | MXDA | MXDA | MXDA | MXDA | MXDA | MXDA |
| | Molar ratio of diamine/styrene | 1/1 | 1/1 | 1/1 | 1/1 | 1/1 | 1/1 | 1/1 |
| | Catalyst 1 | $NaNH_2$ | $NaNH_2$ | $NaNH_2$ | $NaNH_2$ | $NaNH_2$ | $NaNH_2$ | $NaNH_2$ |
| | (% by mass)*[1] | 0.68 | 1.0 | 1.0 | 1.0 | 1.0 | 1.0 | 1.0 |
| | (mol %)*[1] | 2.1 | 3.1 | 3.1 | 3.1 | 3.1 | 3.1 | 3.1 |
| | Catalyst 2 | KOtBu | KOtBu | KOtBu | KOtBu | KOtBu | KCl | KOH |
| | (% by mass)*[1] | 1.95 | 2.9 | 5.8 | 1.4 | 1.9 | 3.8 | 1.4 |
| | (mol %)*[1] | 2.1 | 3.1 | 6.2 | 1.5 | 3.1 | 6.2 | 3.1 |
| | Content (mol %) of potassium when a content of the entire alkali metal in the catalyst is taken as 100 mol % | 50 | 50 | 67 | 33 | 50 | 67 | 50 |
| | Preliminary reaction temperature (° C.) | 80 | 80 | 80 | 80 | 80 | 80 | 80 |
| | Styrene dropping temperature (° C.) | 80 | 80 | 80 | 80 | 80 | 80 | 80 |
| | Method for adding catalyst | All at once | All at once | All at once | All at once | All at once | All at once | All at once |
| Analysis result | Amine composition | A | B | C | D | E | F | G |
| | Styrene reaction rate (%) | 100 | 100 | 85 | 100 | 100 | 100 | 55 |
| | Content (% by mass) of Compound (1) | 38.2 | 53.5 | — | 51.5 | 29.5 | 31.3 | — |
| | (1)/[(1) + (2)] (% by mass) | 67 | 81 | 86 | 78 | 50 | 53 | 58 |
| | 1/2/3 adduct ratio | 57/36/7 | 66/33/1 | — | 66/33/1 | 59/35/6 | 59/35/6 | — |
| | AHEW | 81 | 78 | — | 74*[2] | 88*[2] | 86*[2] | — |
| | Viscosity (mPa · s) 25° C. | 218 | 422 | — | — | — | — | — |
| | Gardener color scale | — | — | — | — | — | — | — |

| | | Example | | | | | |
|---|---|---|---|---|---|---|---|
| | | A-8 | A-9 | A-10 | A-11 | A-12 | A-13 |
| Production conditions | Diamine | MXDA | MXDA | MXDA | MXDA | MXDA | MXDA |
| | Molar ratio of diamine/styrene | 1/1 | 1/1 | 1/1 | 1/1 | 1/1 | 1/1 |
| | Catalyst 1 | $LiNH_2$ | $NaNH_2$ | $NaNH_2$ | $NaNH_2$ | $NaNH_2$ | $NaNH_2$ |
| | (% by mass)*1 | 0.2 | 0.68 | 0.68 | 0.68 | 0.5 | 0.5 |
| | (mol %)*[1] | 1.0 | 2.1 | 2.1 | 2.1 | 1.5 | 1.5 |
| | Catalyst 2 | KOtBu | KOtBu | KOtBu | KOtBu | KOtBu | KOtBu |
| | (% by mass)*1 | 0.98 | 0.49 | 0.49 | 0.49 | 0.72 | 0.72 |
| | (mol %)*[1] | 1.0 | 0.53 | 0.53 | 0.53 | 0.77 | 0.77 |
| | Content (mol %) of potassium when a content of the entire alkali metal in the catalyst is taken as 100 mol % | 50 | 20 | 20 | 20 | 34 | 34 |
| | Preliminary reaction temperature (° C.) | 80 | 80 | 80 | 70 | 80 | 80 |
| | Styrene dropping temperature (° C.) | 80 | 80 | 80 | 70 | 80 | 80 |
| | Method for adding catalyst | | All at once | All at once | All at once | All at once | Dividedly |
| Analysis result | Amine composition | H | I | J | K | L | M |
| | Styrene reaction rate (%) | | 100 | 100 | 100 | 83 | 100 |
| | Content (% by mass) of Compound (1) | 20.7 | 41.2 | 36.6 | 37.2 | 39.3 | 42.8 |
| | (1)/[(1) + (2)] (% by mass) | 39 | 71 | 61 | 63 | 69 | 75 |
| | 1/2/3 adduct ratio | 53/40/7 | 58/36/6 | 60/35/5 | 59/35/6 | 57/36/7 | 57/37/6 |
| | AHEW | 91 | 79 | 83*[2] | 84*[2] | 80 | 80 |
| | Viscosity (mPa · s) 25° C. | 174 | 187 | — | — | 197 | 180 |
| | Gardener color scale | — | — | — | — | 6.5 | 3.2 |

*[1]Addition amount based on 100% by mass (100 mol %) of the total amount of diamine and styrene
*[2]Calculated from GC measurement value of composition
*3: "—" means not measured Examples B-1 to B-3: Preparation and Evaluation (1) of Epoxy Resin Composition Next, by using Amine Compositions A, B, and H obtained in Examples A-1, A-2, and A-8 as an epoxy resin curing agent, epoxy resin compositions were produced in the following manner, and the pot life and the appearance, the curing rate, the pencil hardness, the water resistance spot test and the chemical resistance of the coating film were evaluated at 23° C. and 50% R.H. (Evaluation 1).

[Evaluation 1: Evaluation at 23° C. and 50% R.H.]

(Preparation of Epoxy Resin Composition)

An epoxy resin having a glycidyloxy group derived from bisphenol A ("jER828" manufactured by Mitsubishi Chemical Corporation, epoxy equivalent weight: 186 g/equivalent weight, and solid content concentration: 100% by mass) was used as an epoxy resin which is the main agent. With 100 parts by mass of the main agent, each of the amine compositions obtained in Examples A-1, A-2, and A-8 was blended such that the number of active hydrogens in the amine composition and the number of epoxy groups in the epoxy resin became equimolar, and stirred, thereby obtaining an epoxy resin composition. The blending ratio of the epoxy resin composition used in Evaluation 1 is shown in Table 2.

(Evaluation of Pot Life of Epoxy Resin Composition)

50 g of the epoxy resin composition was placed in a cup made of polypropylene and kept under the conditions of 23° C. and 50% R.H., and the time to reach the maximum exothermic temperature was measured. The results are shown in Table 2.

(Appearance of Coating Film)

The epoxy resin composition was applied onto a zinc phosphate-treated iron plate (manufactured by PALTECH Co., Ltd.; SPCC-SD PB-N144 0.8×70×150 mm), which is a substrate, under the conditions of 23° C. and 50% R.H., by using an applicator, thereby forming a coating film (thickness immediately after application: 200 μm). The appearance of the obtained coating film after one day was observed visually to evaluate transparency, smoothness and glossiness according to the following criteria.

<Transparency>

Ex: There is no turbidity.

G: There is slight turbidity, but there is no problem with use.

P: There is white turbidity.

<Smoothness>

Ex: There is no unevenness.

G: There is slight unevenness, but there is no problem with use.

P: There is unevenness.

<Glossiness>

Ex: There is gloss.

G: The gloss slightly deteriorates, but there is no problem with use.

P: There is no gloss.

(Curing Rate)

The epoxy resin composition was applied onto a glass plate (manufactured by Taiyu Machinery Co., Ltd., 25×348× 2.0 mm) under the conditions of 23° C. and 50% R.H., by using an applicator of 76 μm, thereby forming a coating film. The glass plate on which the coating film was formed was set on a paint drying time measuring instrument (manufactured by Taiyu Machinery Co., Ltd.), the striations when the needle of the measuring instrument scratched the surface of the coating film were observed, and the time to reach each drying step (finger contact drying, half-drying, and complete drying) was measured according to the following criteria. The results are shown in Table 2. A shorter time indicates a higher curing rate.

<Curing Rate>

Finger contact drying: time taken until when the traces of the needle start to remain on the glass plate Half-drying: time taken until when the needle emerges from the middle of the coating film onto the surface of the coating film Complete drying: time taken until when no traces of the needle remain on the coating film (Pencil Hardness)

An epoxy resin composition was applied onto a substrate (zinc phosphate-treated iron plate) in the same manner as described above to form a coating film (thickness immediately after application: 200 μm). This coating film was kept under the conditions of 23° C. and 50% R.H., and after 1, 3, and 7 days passed, the pencil hardness was measured in accordance with JIS K5600-5-4:1999. The results are shown in Table 2.

(Water Resistance Spot Test)

An epoxy resin composition was applied onto a substrate (zinc phosphate-treated iron plate) in the same manner as described above to form a coating film (thickness immediately after application: 200 μm). This coating film was kept under the conditions of 23° C. and 50% R.H., and after 1, 3, and 7 days passed, 2 to 3 drops of pure water were dropped on the surface of the coating film with a dropper, and the portion was covered with a 50 mL screw tube bottle. After 24 hours passed, water was wiped off, and the appearance was observed visually and evaluated according to the following criteria. The results are shown in Table 2.

Ex: There is no change.

G: There is a slight change, but the appearance is good.

P: There is a change.

(Chemical Resistance Test)

A coating film was formed (thickness immediately after coating: 200 μm) by applying an epoxy resin composition on a substrate (zinc phosphate-treated iron plate) in the same manner as described above, and the coating film in which a non-coating part was sealed with a rust preventive paint (a million primer manufactured by Kansai Paint Co., Ltd., million clear) was used as a test specimen. The chemicals used are as shown in Table 2. This test specimen was kept under the conditions of 23° C. and 50% R.H., and after 14 days passed, the chemical resistance of the test specimen was evaluated.

For the salt water spray test, after the test specimen was placed in a salt water spray tester ("STP-90" manufactured by Suga Test Instruments Co., Ltd., in-bath temperature 35° C.), and continuously sprayed with salt water (concentration 5% by mass) for 4 weeks, the appearance thereof was observed visually and evaluated according to the following criteria.

Ex: There is no change.

G: There is a slight change, but the appearance is good.

P: There is a change.

Further, for chemical immersion tests other than salt water, each chemical shown in Table 2 was formulated and poured into a 1 L poly container, the test specimen was immersed up to about 80 mm and kept under the condition of 23° C. for 4 weeks, and then the appearance thereof was observed visually and evaluated according to the following criteria.

Ex: There is no change.

G: There is a slight change, but the appearance is good.

F: There is a change.

TABLE 2

|  |  | Example | | |
|---|---|---|---|---|
|  |  | B-1 | B-2 | B-3 |
| Curing agent | Amine composition | A | B | H |
|  | Content (% by mass) of Compound (1) | 38.2 | 53.5 | 20.7 |
|  | (1)/[(1) + (2)] (% by mass) | 67 | 81 | 39 |
|  | AHEW | 81 | 78 | 91 |
|  | Blending amount (g) in epoxy resin composition | 44 | 42 | 49 |
| Main agent | Type | jER828 | jER828 | jER828 |
|  | Blending amount (g) in epoxy resin composition | 100 | 100 | 100 |
| Pot life (min) |  | 425 | 378 | 438 |
| Coating film appearance (transparency/smoothness/glossiness) |  | Ex/Ex/Ex | Ex/Ex/Ex | Ex/Ex/Ex |
| Curing rate | Finger contact drying (time:min) | 4:15 | 4:30 | 6:00 |
|  | Half-drying (time:min) | 7:00 | 7:00 | 7:15 |
|  | Complete drying (time:min) | 13:25 | 9:15 | 17:45 |
| Pencil hardness | After 1/3/7 days passed | H/H/H | H/H/H | H/H/H |
| Water resistance spot test | After 1/3/7 days passed | Ex/Ex/Ex | Ex/Ex/Ex | Ex/Ex/Ex |
| Chemical resistance test | Salt water spray | Ex | Ex | Ex |
|  | Water | Ex | Ex | Ex |
|  | 10% by mass of aqueous methanol solution | Ex | Ex | Ex |
|  | Methanol | G | G | G |
|  | Toluene | F | F | G |
|  | 10% by mass of aqueous NaOH solution | Ex | Ex | Ex |
|  | 10% by mass of aqueous sulfuric acid solution | G | G | G |

Examples C-1 and C-2: Preparation and Evaluation (Evaluation 2) of Epoxy Resin Composition Next, by using Amine Compositions A and H obtained in Examples A-1 and A-8 as an epoxy resin curing agent, epoxy resin compositions were produced in the following manner, and the appearance, the curing rate, the pencil hardness, and the water resistance spot test of the coating film were evaluated under the low-temperature conditions of 10° C. and 80% R.H. (Evaluation 2).

[Evaluation 2: Evaluation at 10° C. and 80% R.H.]
(Preparation of Epoxy Resin Composition)

An epoxy resin having a glycidyloxy group derived from bisphenol F ("jER 807" manufactured by Mitsubishi Chemical Corporation, epoxy equivalent weight: 169 g/equivalent weight, and solid content concentration: 100% by mass) was used as an epoxy resin which is the main agent. With 100 parts by mass of the main agent, each of the amine compositions obtained in Examples A-1 and A-8 was blended such that the number of active hydrogens in the amine composition and the number of epoxy groups in the epoxy resin became equimolar, and stirred, thereby obtaining an epoxy resin composition. The blending ratio of the epoxy resin composition used in Evaluation 2 is shown in Table 3.

Further, the appearance, the curing speed, the pencil hardness, and the water resistance spot test of the coating film were evaluated in the same manner as in Evaluation 1, except that the evaluation conditions were changed to the conditions of 10° C. and 80% R.H. The results are shown in Table 3.

TABLE 3

|  |  | Example | |
|---|---|---|---|
|  |  | C-1 | C-2 |
| Curing agent | Amine composition | A | H |
|  | Content (% by mass) of Compound (1) | 38.2 | 20.7 |
|  | (1)/[(1) + (2)] (% by mass) | 67 | 39 |
|  | AHEW | 81 | 91 |
|  | Blending amount (g) in epoxy resin composition | 48 | 54 |
| Main agent | Type | jER807 | jER807 |
|  | Blending amount (g) in epoxy resin composition | 100 | 100 |
| Coating film appearance (transparency/smoothness/glossiness) |  | Ex/Ex/Ex | Ex/Ex/Ex |
| Curing rate | Finger contact drying (time:min) | 7:30 | 8:00 |
|  | Half-drying (time:min) | 14:30 | 14:00 |
|  | Complete drying (time:min) | 17:30 | 18:30 |

TABLE 3-continued

|  |  | Example | |
|---|---|---|---|
|  |  | C-1 | C-2 |
| Pencil hardness | After 1/3/7 days passed | H/H/H | H/H/H |
| Water resistance spot test | After 1/3/7 days passed | Ex/Ex/Ex | Ex/Ex/Ex |

As described above, it can be seen that the amine compound and the amine composition of the present invention are useful as an epoxy resin curing agent, and the epoxy resin composition including the epoxy resin curing agent and the cured product thereof exhibit good performance.

Examples D-1 to D-5: Preparation and Evaluation (Evaluation 3) of Epoxy Resin Composition An epoxy resin composition was produced in the following manner by using, as an epoxy resin curing agent, a mixture of Amine Composition M obtained in Example A-13 and the reaction product ("GASKAMINE 328" manufactured by Mitsubishi Gas Chemical Company, Inc., AHEW 55) of MXDA and epichlorohydrin, which is the polyamine modified product (i-1), and the appearance, the curing rate, the finger touch drying, the pencil hardness, and the water resistance spot test of the coating film were evaluated under the conditions of 23° C. and 50% R.H. (Evaluation 3).

[Evaluation 3: Evaluation at 23° C. and 50% R.H.]
(Preparation of Epoxy Resin Composition)

Example D-1

An epoxy resin having a glycidyloxy group derived from bisphenol A ("jER 828" manufactured by Mitsubishi Chemical Corporation, epoxy equivalent weight: 186 g/equivalent weight, and solid content concentration: 100% by mass) was used as an epoxy resin which is the main agent. With 100 parts by mass of the main agent, Amine Composition M obtained in Examples A-13 was blended such that the number of active hydrogens in the amine composition and the number of epoxy groups in the epoxy resin became equimolar, and stirred, thereby obtaining an epoxy resin composition.

Examples D-2 to D-5

Amine Composition M and GASKAMINE328 were mixed at the blending ratio shown in Table 4. Epoxy resin compositions were produced in the same manner as in Example D-1, except that the mixture was used as an epoxy resin curing agent.

The blending ratios of the epoxy resin compositions used in Evaluation 3 are shown in Table 4.

(Appearance of Coating Film)
The epoxy resin composition was applied onto a zinc phosphate-treated iron plate (manufactured by PALTECH Co., Ltd.; SPCC-SD PB-N144 0.8×70×150 mm), which is a substrate, under the conditions of 23° C. and 50% R.H., by using an applicator, thereby forming a coating film (thickness immediately after application: 200 μm). The appearance of the obtained coating film was observed visually to evaluate transparency, smoothness and glossiness according to the following criteria.

<Transparency>
Ex: Excellent (there is no turbidity)
G: Good (there is slight turbidity, but there is no problem with use)
F: Fair (there is slight white turbidity)
P: Poor (white turbidity)
<Smoothness>
Ex: Excellent (there is no unevenness)
G: Good (there is slight unevenness, but there is no problem with use)
F: Fair (there is some unevenness)
P: Poor (there is cissing or unevenness on the whole surface)
<Glossiness>
Ex: Excellent (there is gloss)
G: Good (gloss slightly deteriorates, but there is no problem with use)
F: Fair (less gloss)
P: Poor (there is no gloss)
(Curing Rate)
The epoxy resin composition was applied onto a glass plate (manufactured by Taiyu Machinery Co., Ltd., 25×348× 2.0 mm) under the conditions of 23° C. and 50% R.H., by using an applicator of 76 μm, thereby forming a coating film. The glass plate on which the coating film was formed was set on a paint drying time measuring instrument (manufactured by Taiyu Machinery Co., Ltd.), the striations when the needle of the measuring instrument scratched the surface of the coating film were observed, and the time to reach each drying step (finger contact drying, half-drying, and complete drying) was measured according to the following criteria. The results are shown in Table 4. A shorter time indicates a higher curing rate.
<Curing Rate>
Finger contact drying: time taken until when traces of the needle start to remain on the glass plate
Half-drying: the time taken until when the needle emerges from the middle of the coating film onto the surface of the coating film
Complete drying: time taken until when no traces of the needle remain on the coating film
(Finger Contact Drying)
An epoxy resin composition was applied onto a substrate (zinc phosphate-treated iron plate) in the same manner as described above to form a coating film (thickness immediately after application: 200 μm). This coating film was kept under the conditions of 23° C. and 50% R.H., and after 1, 2, and 7 days passed, the dry state of the coating film was evaluated according to the following criteria. The results are shown in Table 4.
Ex: Excellent (there is no stickiness)
G: Good (slightly sticky)
F: Fair (sticky)
P: Poor (very sticky)
(Pencil Hardness)
An epoxy resin composition was applied onto a substrate (zinc phosphate-treated iron plate) in the same manner as described above to form a coating film (thickness immediately after application: 200 μm). This coating film was kept under the conditions of 23° C. and 50% R.H., and after 1, 2, and 7 days passed, the pencil hardness was measured in accordance with JIS K5600-5-4:1999. The results are shown in Table 4.

(Water Resistance Spot Test)

An epoxy resin composition was applied onto a substrate (zinc phosphate-treated iron plate) in the same manner as described above to form a coating film (thickness immediately after application: 200 μm). This coating film was kept under the conditions of 23° C. and 50% R.H., and after 1, 2, and 7 days passed, 2 to 3 drops of pure water were dropped on the surface of the coating film with a dropper, and the portion was covered with a 50 mL screw tube bottle. After 24 hours passed, water was wiped off, and the appearance was observed visually and evaluated according to the following criteria. The results are shown in Table 4.

Ex: Excellent (there is no trace of water drops)
G: Good (there are slight traces of water drops)
F: Fair (there are traces of water drops)
P: Poor (there are traces of water drops spreading)

[Evaluation 4: Evaluation at 23° C. and 50% R.H.]
(Preparation of Epoxy Resin Composition)

Example E-1

An epoxy resin having a glycidyloxy group derived from bisphenol A ("jER 828" manufactured by Mitsubishi Chemical Corporation, epoxy equivalent weight: 186 g/equivalent weight, and solid content concentration: 100% by mass) was used as an epoxy resin which is the main agent. With 100 parts by mass of this main agent, Amine Composition M obtained in Example A-13 and a benzyl alcohol dilution product ("Ancamine 1618" manufactured by AIR PRODUCTS Co., Ltd.) of the reaction product of isophorone diamine and bisphenol A diglycidyl ether, which corresponds to the polyamine modified product (i-2), were mixed at the blending ratio shown in Table 5. An epoxy resin composition was produced in the same manner as in

TABLE 4

| | | Example | | | | |
|---|---|---|---|---|---|---|
| | | D-1 | D-2 | D-3 | D-4 | D-5 |
| Curing agent | Amine Composition M (parts by mass) | 100 | 90 | 80 | 70 | 50 |
| | GASKAMINE328 (parts by mass) | 0 | 10 | 20 | 30 | 50 |
| | Blending amount (g) in epoxy resin composition | 43 | 41 | 39 | 38 | 35 |
| | AHEW | 80 | 76 | 73 | 70 | 65 |
| Main agent | Type | jER828 | jER828 | jER828 | jER828 | jER828 |
| | Blending amount (g) in epoxy resin composition | 100 | 100 | 100 | 100 | 100 |
| Solid content (% by mass) of epoxy resin composition | | 100 | 100 | 100 | 100 | 100 |
| Coating film appearance (transparency/smoothness/glossiness) | | Ex/Ex/Ex | Ex/Ex/Ex | Ex/Ex/Ex | Ex/Ex/Ex | Ex/Ex/Ex |
| Curing rate | Finger contact drying (time:min) | 4:15 | 3:45 | 2:45 | 2:45 | 2:30 |
| | Half-drying (time:min) | 7:30 | 6:15 | 4:15 | 3:30 | 3:15 |
| | Complete drying (time:min) | 19:00 | 20:00 | 20:00 | 19:45 | 19:30 |
| Finger contact drying | After 1/2/7 days passed | Ex/Ex/Ex | Ex/Ex/Ex | Ex/Ex/Ex | Ex/Ex/Ex | G/G/Ex |
| Pencil hardness | After 1/2/7 days passed | H/H/H | H/H/H | H/H/H | H/H/H | H/H/H |
| Water resistance spot test | After 1/2/7 days passed | Ex/Ex/Ex | Ex/Ex/Ex | F/F/G | P/P/P | P/P/P |

As shown in Table 4, it can be seen that an epoxy resin composition using an epoxy resin curing agent containing an amine composition containing the amine compound of the present invention and a reaction product of MXDA and epichlorohydrin (the polyamine modified product (i-1)) has particularly a fast half-drying time and thus exhibits good curability.

Examples E-1 and E-2: Preparation and Evaluation (Evaluation 4) of Epoxy Resin Composition An epoxy resin composition was produced in the following manner by using, as an epoxy resin curing agent, a mixture of Amine Composition M obtained in Example A-13 and a polyamine modified product to be described below, and the appearance, the curing rate, the finger touch drying, the pencil hardness, and the water resistance spot test of the coating film were evaluated under the conditions of 23° C. and 50% R.H. (Evaluation 4).

Example D-1, except that the mixture was used as an epoxy resin curing agent.

Example E-2

An epoxy resin composition was produced in the same manner as in Example E-1, except that in Example E-1, a Mannich reaction product ("EH-451K" manufactured by ADEKA Corporation) of metaxylylene diamine, p-tert-butylphenol, and formaldehyde, which corresponds to the polyamine modified product (ii), was used instead of Ancamine 1618.

The blending ratio of the epoxy resin composition used in Evaluation 4 is shown in Table 5.

The appearance, the curing rate, the finger contact drying, the pencil hardness, and the water resistance spot test of the coating film were evaluated in the same manner as in Evaluation 3, except that the epoxy resin composition was used. The results are shown in Table 5.

TABLE 5

| | | Example E-1 | Example E-2 |
|---|---|---|---|
| Curing agent | Amine Composition M (parts by mass) | 50 | 50 |
| | Ancamine 1618 (parts by mass) | 50 | 0 |
| | EH-451K (parts by mass) | 0 | 50 |
| | Blending amount (g) in epoxy resin composition | 50 | 42 |
| | AHEW | 94 | 79 |
| Main agent | Type | jER828 | jER828 |
| | Blending amount (g) in epoxy resin composition | 100 | 100 |
| Solid content (% by mass) of epoxy resin composition | | 100 | 100 |
| Coating film appearance (transparency/smoothness/glossiness) | | Ex/Ex/Ex | Ex/Ex/Ex |
| Curing rate | Finger contact drying (time:min) | 2:00 | 1:30 |
| | Half-drying (time:min) | 4:00 | 2:30 |
| | Complete drying (time:min) | 13:00 | >24 |
| Finger contact drying | After 1/2/7 days passed | Ex/Ex/Ex | Ex/Ex/Ex |
| Pencil hardness | After 1/2/7 days passed | H/H/H | H/H/H |
| Water resistance spot test | After 1/2/7 days passed | G/G/G | G/G/G |

As shown in Table 5, the epoxy resin composition using the epoxy resin curing agent containing the amine composition including the amine compound of the present invention and Ancamine 1618 (polyamine modified product (i-2)) had a high curing rate (Example E-1). It can be seen that the epoxy resin composition using the epoxy resin curing agent containing the amine composition including the amine compound of the present invention and the epoxy resin curing agent containing EH-451K (polyamine modified product (ii)) had particularly a fast finger contact drying time and a fast half-drying time (Example E-2), and thus exhibits good curability.

Examples F-1 and F-2: Preparation and Evaluation (Evaluation 5) of Epoxy Resin Composition An epoxy resin composition was produced in the following manner by using Amine Composition M obtained in Example A-13 and a curing accelerator, and the appearance, the curing rate, the finger touch drying, the pencil hardness, and the water resistance spot test of the coating film were evaluated under the conditions of 23° C. and 50% R.H. (Evaluation 5).

[Evaluation 5: Evaluation at 23° C. and 50% R.H.]
(Preparation of Epoxy Resin Composition)

Example F-1

An epoxy resin having a glycidyloxy group derived from bisphenol A ("jER 828" manufactured by Mitsubishi Chemical Corporation, epoxy equivalent weight: 186 g/equivalent weight, and solid content concentration: 100% by mass) was used as an epoxy resin which is the main agent. With 100 parts by mass of the main agent, Amine Composition M obtained in Example A-13 and salicylic acid, which is Curing Accelerator 1, were mixed at the blending ratio shown in Table 6. An epoxy resin composition was produced in the same manner as in Example D-1, except that the mixture was used as an epoxy resin curing agent.

Example F-2

By using a styrenated phenol ("Kumanox-3110(MSP)" manufactured by KUMHO PETROCHEMICAL Co., Ltd., average molecular weight: 220), which is Curing Accelerator 2, instead of salicylic acid in Example F-1, Amine Composition M and the styrenated phenol were mixed at the blending ratio shown in Table 6. An epoxy resin composition was produced in the same manner as in Example F-1, except that the mixture was used as an epoxy resin curing agent.

The mixing ratio of the epoxy resin composition used in Evaluation 5 is shown in Table 6.

Kumanox-3110(MSP) is a styrenated phenol represented by the following structural formula, and m=1 to 3.

[Chem. 13]

The appearance, the curing rate, the finger contact drying, the pencil hardness, and the water resistance spot test of the coating film were evaluated in the same manner as in Evaluation 3, except that the epoxy resin composition was used. The results are shown in Table 6.

TABLE 6

| | | Example | | |
|---|---|---|---|---|
| | | D-1 | F-1 | F-2 |
| Curing agent | Amine Composition M (parts by mass) | 100 | 95 | 90 |
| | Curing Accelerator 1: Salicylic acid (parts by mass) | 0 | 5 | 0 |

TABLE 6-continued

|  |  | Example | | |
|---|---|---|---|---|
|  |  | D-1 | F-1 | F-2 |
|  | Curing Accelerator 2: Styrenated phenol (parts by mass) | 0 | 0 | 10 |
|  | Blending amount (g) in epoxy resin composition | 43 | 45 | 48 |
|  | AHEW | 80 | 84 | 89 |
| Main agent | Type | jER828 | jER828 | jER828 |
|  | Blending amount (g) in epoxy resin composition | 100 | 100 | 100 |
| Solid content (% by mass) of epoxy resin composition |  | 100 | 100 | 100 |
| Coating film appearance (transparency/smoothness/glossiness) |  | Ex/Ex/Ex | Ex/Ex/Ex | Ex/Ex/Ex |
| Curing rate | Finger contact drying (time:min) | 4:15 | 2:30 | 3:30 |
|  | Half-drying (time:min) | 7:30 | 4:15 | 5:30 |
|  | Complete drying (time:min) | 19:00 | 17:15 | 8:30 |
| Finger contact drying | After 1/2/7 days passed | Ex/Ex/Ex | Ex/Ex/Ex | Ex/Ex/Ex |
| Pencil hardness | After 1/2/7 days passed | H/H/H | H/H/H | H/H/H |
| Water resistance spot test | After 1/2/7 days passed | Ex/Ex/Ex | Ex/Ex/Ex | Ex/Ex/Ex |

Example G-1: Preparation and Evaluation (Evaluation 6) of Water-Based Epoxy Resin Composition An epoxy resin composition was produced in the following manner by using Amine Composition M obtained in Example A-13 as a curing agent for a water-based epoxy resin, and the appearance, the curing rate, the finger touch drying, the pencil hardness, and the water resistance spot test of the coating film were evaluated under the conditions of 23° C. and 50% R.H. (Evaluation 6).

[Evaluation 6: Evaluation at 23° C. and 50% R.H.] (Preparation of Epoxy Resin Composition)

Example G-1

A water-based emulsion (manufactured by Mitsubishi Chemical Corporation, epoxy equivalent weight in an emulsion state: 1,020 g/equivalent weight, epoxy resin concentration: 50% by mass, water content: 45% by mass, and content of other components (emulsifier, and the like): 5% by mass) of a solid epoxy resin having a glycidyloxy group derived from bisphenol A was used as a water-based epoxy resin which is the main agent. With 100 parts by mass of the main agent, Amine Composition M obtained in Examples A-13 was blended such that the number of active hydrogens in the amine composition and the number of epoxy groups in the water-based epoxy resin became equimolar, and stirred thereby obtaining a water-based epoxy resin composition.

Reference Example G-1

A water-based epoxy resin composition was obtained in the same manner as in Example G-1, except that in Example G-1, a commercially available adduct ("GASKAMINE240" manufactured by Mitsubishi Gas Chemical Company, Inc., AHEW 103) of metaxylylene diamine and styrene was used instead of Amine Composition M.

The blending ratio of the water-based epoxy resin composition used in Evaluation 6 is shown in Table 7.

The appearance, the curing rate, the finger contact drying, the pencil hardness, and the water resistance spot test of the coating film were evaluated in the same manner as in Evaluation 3, except that the water-based epoxy resin composition was used. The results are shown in Table 7.

TABLE 7

|  |  | Example G-1 | Reference Example G-1 |
|---|---|---|---|
| Curing agent | Amine Composition M (parts by mass) | 100 | 0 |
|  | GASKAMINE240 (parts by mass) | 0 | 100 |
|  | Blending amount (g) in epoxy resin composition | 7.8 | 10 |
| Main agent | Type | W1155R55 | W1155R55 |
|  | Blending amount (g) in epoxy resin composition | 100 | 100 |
| Solid content (% by mass) of epoxy resin composition |  | 58 | 59 |
| Coating film appearance (transparency/smoothness/glossiness) |  | Ex/F/Ex | Ex/F/Ex |
| Curing rate | Finger contact drying (time:min) | 0:01 | 0:01 |
|  | Half-drying (time:min) | 0:30 | 1:15 |
|  | Complete drying (time:min) | 8:30 | 6:30 |

TABLE 7-continued

| | | Example G-1 | Reference Example G-1 |
|---|---|---|---|
| Finger contact drying | After 1/2/7 days passed | Ex/Ex/Ex | Ex/Ex/Ex |
| Pencil hardness | After 1/2/7 days passed | H/H/H | H/H/H |
| Water resistance spot test | After 1/2/7 days passed | F/G/Ex | Ex/Ex/Ex |

As shown in Table 7, it can be seen that the amine compound and the amine composition of the present invention are also useful as a curing agent for a water-based epoxy resin, and good performance is exhibited as in the case of using a commercially available epoxy resin curing agent.

INDUSTRIAL APPLICABILITY

According to the present invention, by using an amine compound having a specific structure and an amine composition containing the same as an epoxy resin curing agent, even though an amount of epoxy resin curing agent blended in the epoxy resin composition is small, the epoxy resin curing agent has sufficient curability, so that it is possible to provide a cured product having good properties. The epoxy resin composition is suitably used for various paints such as a paint for corrosion resistance, an adhesive, a floor material, a sealant, and the like.

The invention claimed is:

1. An amine composition comprising the amine compound represented by the following formula (1):

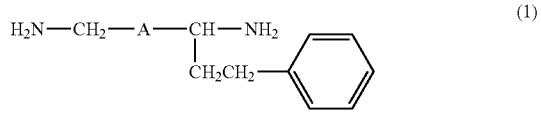

(1)

wherein A is a 1,2-phenylene group, a 1,3-phenylene group, or a 1,4-phenylene group, wherein the amine composition is obtained by a method comprising:
subjecting a diamine represented by the following formula (3) and styrene to addition reaction in the presence of an alkali metal-containing catalyst comprising the following (c2):

$$H_2N-CH_2\text{-}A\text{-}CH_2-NH_2 \quad (3)$$

wherein A is the same as defined above;
(c2): a combination of an alkali metal amide with one or more selected from the group consisting of an alkali metal alkoxide, an alkali metal hydroxide, an alkali metal halide, and an alkali metal nitrate.

2. The amine composition according to claim 1, further comprising an amine compound represented by the following formula (2):

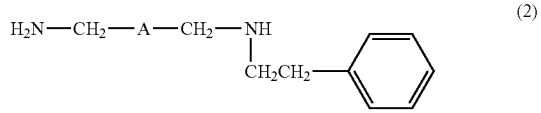

(2)

wherein A is the same as defined above.

3. The amine composition according to claim 2, wherein a content of the amine compound represented by the formula (1) is 15% by mass or more and less than 100% by mass based on 100% by mass of the total amount of the amine compound represented by the formula (1) and the amine compound represented by the formula (2).

4. A method for preparing the amine composition according to claim 1, the method comprising:
subjecting a diamine represented by the following formula (3) and styrene to addition reaction in the presence of an alkali metal-containing catalyst and comprising the following (c2):

$$H_2N-CH_2\text{-}A\text{-}CH_2-NH_2 \quad (3)$$

wherein A is the same as defined above; and
(c2): a combination of an alkali metal amide with one or more selected from the group consisting of an alkali metal alkoxide, an alkali metal hydroxide, an alkali metal halide, and an alkali metal nitrate.

5. The method according to claim 4, wherein the alkali metal amide in the (c2) is one or more selected from the group consisting of sodium amide and potassium amide.

6. The method according to claim 4, wherein the (c2) is a combination of an alkali metal amide with an alkali metal alkoxide, and the alkali metal alkoxide is potassium t-butoxide.

7. The method according to claim 4, wherein the alkali metal-containing catalyst is added portionwise in the addition reaction.

8. An epoxy resin curing agent comprising the amine composition according to claim 1.

9. The epoxy resin curing agent according to claim 8, further comprising a modified product of a polyamine compound as an additional curing agent component.

10. The epoxy resin curing agent according to claim 8, further comprising a curing accelerator.

11. The epoxy resin curing agent according to claim 8, which is a curing agent for a water-based epoxy resin.

12. An epoxy resin composition comprising the epoxy resin curing agent according to claim 8 and an epoxy resin.

13. A paint comprising the epoxy resin composition according to claim 12.

14. An adhesive comprising the epoxy resin composition according to claim 12.

15. A cured product of the epoxy resin composition according to claim 12.

* * * * *

UNITED STATES PATENT AND TRADEMARK OFFICE
CERTIFICATE OF CORRECTION

PATENT NO. : 10,941,242 B2
APPLICATION NO. : 16/090998
DATED : March 9, 2021
INVENTOR(S) : S. Sato et al.

Page 1 of 1

It is certified that error appears in the above-identified patent and that said Letters Patent is hereby corrected as shown below:

In the Claims

At Column 48, Line 11, (Claim 4, Line 5), please delete "and" before comprising.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*